United States Patent
Williams et al.

(10) Patent No.: US 11,084,794 B2
(45) Date of Patent: Aug. 10, 2021

(54) CONTROLLED CYCLIZATION OF PEPTOIDS TO FORM CHIRAL DIKETOPIPERAZINES

(71) Applicant: Triad National Security, LLC, Los Alamos, NM (US)

(72) Inventors: Robert F. Williams, Los Alamos, NM (US); Paul William Peterson, Los Alamos, NM (US); Robert David Gilbertson, Los Alamos, NM (US); Jurgen G. Schmidt, Los Alamos, NM (US); Charlie E. Strauss, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 16/668,444

(22) Filed: Oct. 30, 2019

(65) Prior Publication Data

US 2020/0131140 A1 Apr. 30, 2020

Related U.S. Application Data

(60) Provisional application No. 62/752,657, filed on Oct. 30, 2018.

(51) Int. Cl.
*C07D 241/08* (2006.01)
(52) U.S. Cl.
CPC .................................. *C07D 241/08* (2013.01)
(58) Field of Classification Search
CPC .................................................. C07D 241/08
See application file for complete search history.

(56) References Cited

U.S. PATENT DOCUMENTS

2011/0144336 A1* 6/2011 Zierke .................. C07D 241/08
544/385

OTHER PUBLICATIONS

Cho, et al. "One-pot synthesis of symmetrical 1,4-disubstituted piperazine-2,5-diones" Korean Chemical Society; 2004; vol. 25; pp. 415-416.
Abu-Shanab, et al. "Synthesis of 1,4-diaryl-piperazine-2,5-diones: new behavior of N,N-dimethylformamide dimethyl acetal (DMFDMA)" Synthetic Communications; 2008; vol. 38; pp. 376-382.
Tadano, et al. "Collective synthesis and biological evaluation of tryptophan-based dimeric diketopiperazine alkaloids" , Chemistry European Journal; 2016; vol. 22; pp. 1277-1291.
Ugi "Novel methods of preparative organic chemistry IV" Angew. Chem. Internat. Edit.; 1962; vol. 1; No. 1; pp. 8-21.
Virgone-Carlotta, et al. "New diketopiperazines as vectors for peptide protection and brain delivery: synthesis and biological evaluation" Journal Labelled Compounds and Radiopharmaceuticals; 2016; vol. 59; pp. 517-530.
Zhang, et al. "Characterization of secondary amide peptide bond isomerization: thermodynamics and kinetics from 2D NMR spectroscopy" Biopolymers; 2011; vol. 95; No. 11; pp. 755-762.
Stewart, et al. "Occurrence and Role of Cis Peptide Bonds in Protein Structures" Journal Molecular Biology; 1990; vol. 214; pp. 253-260.
Jabs, et al. "Non-proline Cis Peptide Bonds in Proteins" Journal Molecular Biology; 1999; vol. 285; pp. 291-304.
Tullberg, et al. "Efficient synthesis of 2,5-diketopiperazines using microwave assisted heating" Tetrahedreon; 2006; vol. 62; pp. 7484-7491.
Halimehjani, et al. "Synthesis of a novel category of Ugi adducts using succinic acid, succinic anhydride and maleic anhydride and their application in post-Ugi reactions for synthesis of functionalized piperazine" Tetrahedron; 2017; vol. 73; pp. 5778-5783.
Bull, et al. "Practical synthesis of Schollkopf's bis-lactim ether chiral auxiliary: (3S)-3,6-dihydro-2,5-dimethoxy-3-isoproplyl-pryazine" Tetrahedron: Asymmetry; 1998; vol. 9; pp. 321-327.
Liao, et al. "Design, synthesis and cytotoxic activities of novel 2,5-diketopiperazine derivatives" European Journal of Medicinal Chemistry; 2016; vol. 121; pp. 500-509.
Sanchez-Navarro, et al. "Blood-brain barrier peptide shuttles" Current Opinion in Chemical Biology; 2017; vol. 38; pp. 134-140.
Hulme, et al. "Multi-compnent Reactions: Emerging Chemistry in Drug Discovery" 'From Xylocain to Crixivan' Current Medicinal Chemistry; 2003; vol. 10; pp. 51-80.
Lee, et al. "Convenient asymmetric synthesis of 1,3,4,6-tetrasubstituted 2,5-diketopiperazines" Arkivoc General Papers; 2016; pp. 100-113.
Suzuki, et al. "Acetic Acid-Catalyzed Diketopiperazine Synthesis" Chemical Pharmacy Bull.; 1981; vol. 29; No. 1; pp. 233-237.
Highet, et al. "Progress in the Chemistry of Organic Natural Products" Fortschritte Der Chemie Organischer Naturstoffe; 1975; vol. 32; 568 pages.
Kunz, et al. "Stereoselective syntheses using carbohydrates as chiral auxiliaries" Pure & Appl. Chem.; 1995; vol. 67; No. 10; pp. 1627-1635.
Sanchez-Navarro, et al. "Jumping Hurdles: Peptides able to overcome biological barriers" Accounts of Chemical Research; 2017; vol. 50; pp. 1847-1854.
Jackson, et al. "A- and a-Lithiation-Electrophile trapping of N-Thiopivaloyl and N-tert-Butoxythiocarbonyl x-substituted azetidines: Rationalization of the regiodivergence using NMR and computation" Journal of Organic Chemistry; 2015; vol. 80; pp. 9838-9846.

(Continued)

*Primary Examiner* — Erich A Leeser

(57) ABSTRACT

The present disclosure provides improved methods for controlled cyclization of peptoid dimers to form N,N'-2,5-diketopiperazines (N,N'-2,5-DKPs) with significant selectivity. In at least some examples, selectivity is based on a serendipitous conglomeration of slow exchange of amide rotamers, steric repulsion from the degree of α-substitution, and the geometric bulk of an amine nucleophile. By varying reaction conditions, the selectivity of the reaction and formation of a particular N,N'-2,5-DKP can be switched. The cyclization works in the presence of a variety of protection groups and diverse functionalities. The teachings herein provide techniques for synthesizing N,N'-2,5-DKPs that can be readily docked with drug candidates for shuttling across the blood brain barrier. This method provides a facile way to produce substituted DKPs containing groups ready for post-modification to include docking drug candidates.

20 Claims, 15 Drawing Sheets

(56) References Cited

OTHER PUBLICATIONS

Thakkar, et al. "Cis/Trans Isomerization in secondary amides: reaction paths, nitrogen inversion, and relevance to peptidic systems" The Journal of Physical Chemistry; 2017; vol. 121; pp. 6830-6837.
Kuranaga, et al. "Total Synthesis of Theonellapeptolide Id" Organic Letters; 2017; vol. 19; pp. 1366-1369.
Armstrong, et al. "Multiple-component condensation strategies for combinatorial library synthesis" American Chemical Society; 1996; vol. 29, pp. 123-131.
Lin, et al. "Rapid synthesis of diketopiperazine macroarrays via Ugi four-component reactions on planar solid supports" The Royal Society of Chemistry; Chemistry Communication; 2006; pp. 2884-2886.
Baek, et al. "Asymmetric synthesis of 3,4,6-Trisubstituted 2,5-Diketopiperazines by using dynamic kinetic resolution of x-bromo tertiary acetamindes" European Journal of Organic Chemistry; 2014; pp. 2780-2789.
Miyazawa "Studies of unusual amino acids and their peptides" The Chemical Society of Japan; 1980; vol. 53; pp. 2555-2565.
Suwal, et al. "Solid-phase synthesis of peptoid-like oligomers containing diverse diketopiperazine units" Organic Biomol. Chemistry; 2014; vol. 12; pp. 5831-5834.
Liao, et al. "Design, synthesis and biological evaluation of soluble 2,5-diketopiperazines derivatives as potential antifouling agents" The Royal Society of Chemistry; 2015; vol. 5; pp. 51020-51026.
Oller-Salvia, et al. "Blood-brain barrier shuttle peptides: an emerging paradigm for brain delivery" Chemical Society Review; 2016; vol. 45; pp. 4690-4707.
Sultani, et al. "Spin-labelled diketopiperazines and peptide-peptoid chimera by Ugi-multi-component-reactions" Organic & Biomolecular Chemistry; 2016; vol. 14; pp. 11336-11341.
Cumine, et al. "A study of diketopiperazines as electron-donor initiators in transition metal-free haloarene-arene coupling" Organic & Biomolecular Chemistry; 2017; vol. 15; pp. 3324-3336.
Kelley, et al. "Synthesis of monoalkylidene diketopiperazines and application to the synthesis of barettin" Organic & Biomolecular Chemistry; 2017; vol. 15; pp. 8634-8640.
Borgman, et al. "The expanding spectrum of diketopiperazine natural product biosynthetic pathways containing cyclodipeptide synthases" Organic & Biomolecular Chemistry; 2019; vol. 17; pp. 2305-2314.
Vanommeslaeghe, et al. "Automation of the CHARMM General Force Field (CGenFF) I: Bond Perception and Atom Typing" Journal of Chemical Information and Modeling; 2012; vol. 52; pp. 3144-3154.
Vanommeslaeghe, et al. "Automation of the CHARMM General Force Field (CGenFF) II: Assignment of Bonded Parameters and Partial Atomic Charges" Journal of Chemical Information and Modeling; 2012; vol. 52; pp. 3155-3168.
Borthwick "2,5-Diketopiperazines: Synthesis, Reactions, Medicinal Chemistry, and Bioactive Natural Products" Chemical Reviews; 2012; vol. 112; pp. 3641-3716.
Fryszkowska, et al. "Studies towards the synthesis of bicyclomycin precursors: Synthesis of N,m N1-disubstituted 2,5-diketopiperazines in solution and on solid phase" Journal Heterocyclic Chemical; 2008; vol. 45; p. 765-772.
Laplanche, et al. "cis and trans Configurations of the peptide bond in N-Monosubstituted amides by nuclear magnetic resonance" Kedzie Chemical Laboratory; 1964; p. 337.
Gorske, et al. "Local and tunable n-π* Interactions regulate amide isomerism in the peptoid backbone" Journal American Chemical Society; 2007; vol. 129; pp. 8928-8929.
Teixido, et al. "Diketopiperazines as a tool for the study of transport across the Blood-Brain Barrier (BBB) and their potential use as BBB-Shuttles" Journal American Chemical Society; 2007; vol. 129; pp. 11802-11813.
Codelli, et al. "Enantioselective total synthesis of (−)-acetylaranotin, a dihydrooxepine epidithiodiketopiperazine" Journal American Chemical Society; 2011; vol. 134; pp. 1930-1933.
Laursen, et al. "Cis-Trans amide bond rotamers in B-Peptoids and Peptoids: Evaluation of Stereoelectronic effects in backbone and side chains" Journal American Chemical Society; 2013; vol. 135; pp. 2835-2844.
Renfrew, et al. "A rotamer library to enable modeling and design of peptoid foldamers" Journal American Chemical Society; 2014; vol. 136; pp. 8772-8782.
Scherer, et al. "Barriers to rotation of secondary amide peptide bonds" Journal American Chemical Society; 1998; vol. 120; pp. 5568-5574.
Chen, et al. "Organo-cation catalyzed asymmetric homo/heterodialkylation of bisoxindoles: construction of vicinal all-carbon quaternary stereocenters and total synthesis of (−) chimonanthidine" Journal American Chemical Society; 2018; vol. 140; pp. 10099-10103.
Jainta, et al. "Microwave-assisted stereoselective one-pot synthesis of symmetrical and unsymmetrical 2,5-diketopiperames from unprotected amino acids" European Journal Organic Chemistry; 2008; pp. 5418-5424.
Orena, et al. "Diastereoselective Alkylation of (3S)-and (3R)-3-methylpiperazine-2,5-dione derivatives. A convenient approach to both (S)- and (R)-alanine" Journal Organic Chemistry; 1992; vol. 57; pp. 6532-6536.
Saito, et al. "Theoretical studies on cis-Amide preference in N-Methylanilides" Journal Organic Chemistry; 1995; vol. 60; pp. 4715-4720.
Nitecki, et al. "A simple route to sterically pure diketopiperazines" Journal of Organic Chemistry; 1967; pp. 864-866.
Sollis "Short and novel stereospecific synthesis of trisubstituted 2,5-diketopiperazines" Journal of Organic Chemistry; 2005; vol. 70; pp. 4735-4740.
Tullberg, et al. "Synthesis of functionalized, unsymmetrical 1,3,4,6-tetrasubstituted 2,5-diketopiperazines" Journal of Organic Chemistry; 2007; vol. 72; pp. 195-199.
Nguyen, et al. "Kinetics and equilibria of cis/trans isomerization of secondary amide peptide bonds in linear and cyclic peptides" Journal of Physical Chemistry; 2010; vol. 114; pp. 3387-3392.
Park, et al. "Structural and dynamical characteristics of peptoid oligomers with achiral aliphatic side chains studied by molecular dynamics simulation" Journal of Physical Chemistry; 2011; vol. 115; 10967-10975.
Ma, et al. "Total synthesis and biological evaluation of spirotryprostatin A analogs" Chirality; 2017; vol. 29; pp. 137-746.
Moure, et al. "Chemical modulation of peptoids: synthesis and conformational studies on partially constrained derivatives" Chemistry European Journal; 2011; vol. 17; pp. 7927-7939.
Weiss, et al. Nature Structural Biology; 1998; vol. 5, No. 8; p. 676.

* cited by examiner

General scheme of sub-monomer method of peptoid synthesis with cyclization

CONTROLLED CYCLIZATION OF PEPTOIDS TO FORM CHIRAL DIKETOPIPERAZINES

FEDERALLY SPONSORED RESEARCH OR DEVELOPMENT

The United States government has rights in this invention pursuant to Contract No. 89233218CNA000001 between the United States Department of Energy (DOE), the National Nuclear Security Administration (NNSA), and Triad National Security, LLC for the operation of Los Alamos National Laboratory.

BACKGROUND 2,5-diketopiperazines (2,5-DKPs) are ubiquitous in nature and are products of cyclization of linear dipeptides. They are located in numerous natural products and are highly valued shuttles for passive transport of therapeutic compounds across the blood brain barrier (BBB). 2,5-DKPs are used for therapeutic applications including the prevention of normal mitotic activity in cancer cells and for encapsulation of drugs such as insulin and antibiotics for targeted delivery for diabetes and pneumonia treatments, respectively. 2,5-DKPs are also valuable as antifouling agents and as electron donors for metal-free arene coupling.

Known methods to synthesize 2,5-DKPs utilize either an amide bond formation or a three-component Ugi reaction as the key step (as illustrated in FIG. 1). There are many variations of amide bond formation as the key step in cyclization. One method is through a triggered cyclization through protecting group deprotection on the amine terminus of a dipeptide. Once deprotected, the cyclization occurs spontaneously, and is compatible with many nitrogen protection groups including tert-butyloxycarbonyl (BOC), fluorenylmethyloxycarbonyl chloride (Fmoc), benzyl ether (Bn), and allyloxycarbonyl (Alloc).

Other known methods of 2,5-DKP synthesis utilize in situ cyclization following substitution as well as dimerization. Each of the foregoing known methods has distinct disadvantages in terms of ease of synthesis and maintaining chirality.

Cyclizations to form 2,5-DKPs may be accelerated by acid/base catalysis or by thermal conditions. These accelerative methods sometimes lead to epimerization and loss of chirality, but microwave acceleration lessens the degree of epimerization. Multi-component Ugi reactions in 2,5-DKP synthesis can be stereoselective, but involve multiple preparative chemical steps and are limited by the availability of isocyanides. 2,5-DKPs can also be synthesized through the dimerization of α-haloacyl chlorides, and from in situ cyclization following substitution of α-bromo tertiary acetamides.

There are several applications of 2,5-DKPs. The known synthesis methods described above are used in the synthesis of natural products and to build libraries of 2,5-DKPs for BBB membrane permeability shuttling. 2,5-DKP synthesis has been used in peptoid synthesis to add a bend in the peptoid backbone through heating a pendant amine in the presence of an ester side chain. In this manner, 2,5-DKPs may be incorporated into peptoid backbones in solid phase synthesis.

SUMMARY

The present disclosure provides improved methods for controlled cyclization of peptoid dimers to form N,N'-2,5-diketopiperazines (N,N'-2,5-DKPs) with significant selectivity. Synthesis of N,N'2,5'DKPs, according to the present disclosure, results in successful selective cyclization in the presence of many functional groups, thereby lessening the need of post-modification, which tends to cause epimerization and lose of yield. Experiments suggest cyclization occurs in a diastereoselective manner. Monte Carlo simulations and density functional theory (DFT) optimization studies match experimental selectivity. In at least some examples, peptoid conformations may be defined based on side chain substitution, reaction temperature, and/or addition of non-covalent interactions.

An aspect of the present disclosure relates to a method for controlling cyclization of peptoids to form chiral diketopiperazines, comprising: reacting an acetate ester, comprising a halide or non-halogenated leaving group, with a primary amine to produce a first product having two electrophiles; reacting the first product with a haloacetyl halide to produce a second product; and reacting the second product with an amine nucleophile to produce an N,N'-2,5-diketopiperazine. In at least some examples, the halide is bromine. In at least some examples, the non-halogenated leaving group is either a mesylate or tosylate leaving group. In at least some examples, the acetate ester further comprises at least one of an aliphatic group or an aromatic group. In at least some examples, the at least one of an aliphatic group or an aromatic group comprises at least one of tert-butyl, benzyl, ethyl, or p-tolyl. In at least some examples, the primary amine is selected from the group consisting of an aliphatic primary amine, an aromatic primary amine, an alkenyl primary amine, an alkynyl primary amine, and an acyl primary amine. In at least some examples, a functional group, of the primary amine, is protected using at least one of an ester, tert-butoxyl ester (BOC), benzyloxy carbamate (CBz), a silyl ether, or a pivoloyl ester (Piv). In at least some examples, reacting the acetate ester with the primary amine comprises adding the acetate ester to a solution comprising the primary amine and a tertiary amine. In at least some examples, the tertiary amine comprises at least one of triethylamine, diisopropylamine, imidazole, diisopropylethylamine, or diazabicyclo[2.2.2]octane (DABCO). In at least some examples, the solution comprises a solvent comprising at least one of dichloromethane (DCM), acetonitrile, tetrahydrofuran (THF), or N,N'-dimethylformamide (DMF). In at least some examples, reacting the acetate ester comprises chilling a reaction mixture to about 0° C. In at least some examples, reacting the first product comprises adding the first product to a solution comprising the haloacetyl halide and at least one of pyridine, triethylamine, or diisopropylethylamine. In at least some examples, the haloacetyal halide is selected from the group consisting of bromoacetyl bromide, chloroacetyl chloride, and chloroacetyal bromide. In at least some examples, reacting the first product comprises reacting the first product with a N-hydroxysuccinimide (NHS)-ester of the haloacetyl halide. In at least some examples, reacting the first product comprises adding the first product to a solution comprising the haloacetyl halide and at least one base. In at least some examples, the at least one base comprises at least one of a tertiary amine or an aromatic amine. In at least some examples, reacting the first product comprises chilling a solution, comprising the first product and the haloacetyl halide, to about 0° C. In at least some examples, the method comprises producing a charged intermediate that stirs as a colored slurry in dichloromethane, wherein producing the charged intermediate comprises adding at least one of a tertiary amine or an aromatic amine to a solution comprising the haloacetyl halide, wherein reacting the first product comprises reacting the first product with the charged intermediate to produce the second product. In at least some examples, reacting the first product with the charged intermediate is performed until the colored slurry has disappeared. In at least some examples, the amine nucleophile is a primary amine.

BRIEF DESCRIPTION OF DRAWINGS

For a more complete understanding of the present disclosure, reference is now made to the following description taken in conjunction with the accompanying drawings.

DETAILED DESCRIPTION

Figure 1:
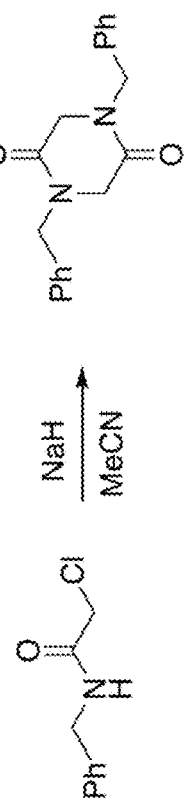
FIG. 1 illustrates known methods to synthesize 2,5-diketopiperazines (2,5-DKPs).
Figure 1:
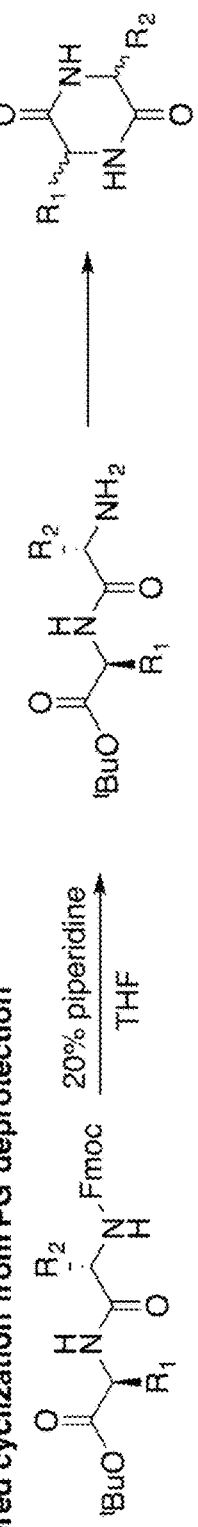
Figure 1:
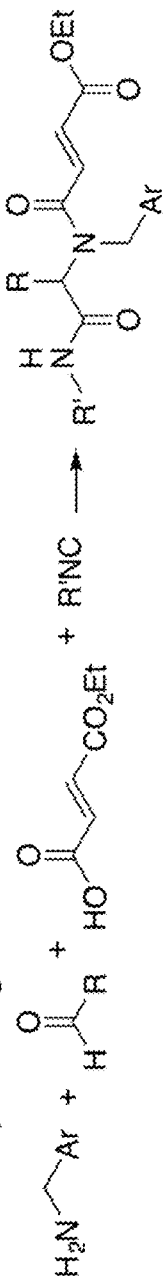
Figure 1:
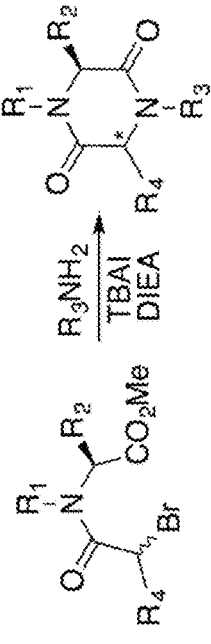

The present disclosure provides improved methods for controlled cyclization of peptoid dimers to form N,N'-2,5-diketopiperazines (N,N'-2,5-DKPs) with significant selectivity. Teachings of the present disclosure provide significant improvement over current methods due to control and lack of the need of post-modification. In at least some examples, selectivity is based on a serendipitous conglomeration of slow exchange of amide rotamers, steric repulsion from the degree of α-substitution, and the geometric bulk of an amine nucleophile. Exploiting these factors have led to the formation of selective, highly functionalized, N,N'-2,5-DKPs. Due to reaction conditions, the selectivity of the reaction can be switched. The cyclization works in the presence of a variety of protection groups and diverse functionalities. The teachings herein provide techniques for synthesizing N,N'-2,5-DKPs that can be readily docked with drug candidates for shuttling across the blood brain barrier. This method provides a facile way to produce substituted DKPs containing groups ready for post-modification to include docking drug candidates.

N,N'-2,5-DKPs

Diketopiperazine is a class of organic compounds related to piperazine but with two amide linkages. 2,5-DKP, in particular, includes a six-membered ring containing two amide linkages, where the two nitrogen atoms and the two carbonyls are at opposite positions in the ring. The following is an example chemical structure of a N,N'-2,5-DKP:

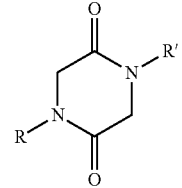

where R and R' are functional groups that may vary depending on desired functionality of the 2,5-DKP. R and R' may be independently selected, meaning R and R' may be the same or different depending on desired characteristics of the 2-5-DKP.

Peptoid Backbone

N,N'-2,5-DKPs of the present disclosure may be cyclized from peptoid dimers. As known in the art, a "dimer" is a molecule, or molecular complex, including two identical molecules linked together. Thus, as used herein, a "peptoid dimer" includes two identical peptoids linked together.

A peptoid is an N-alky or N-aryl glycine polymer having side chains appended to the nitrogen atom of the peptide backbone. This is in contrast to peptides, in which side chains are appended to α-carbons. The following are structures of generic monomers of α-peptide and α-peptoid backbones:

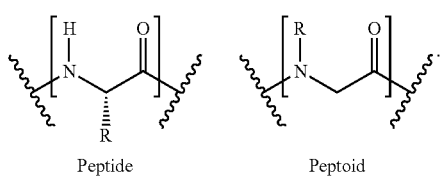

Peptide          Peptoid

Peptoids, unlike peptides, are resistant to hydrolysis under physiological conditions, thereby making N,N'-2,5-DKPs of the present disclosure suitable candidates for in vivo treatment of a subject. As used herein, the term "subject" may refer to a vertebrate mammal including but not limited to a human, non-human primate (e.g., monkey), mouse, rate, guinea pig, rabbit, cow, dog, cat, horse, goat, bird, reptile, or fish. A subject may be a domesticated animal, a wild animal, or an agricultural animal. Accordingly, teachings of the present disclosure may be used with respect to human and non-human subjects. For instance, teachings of the present disclosure can be used in veterinary applications (e.g., in zoos, reserves, farms, in the wild, etc.) as well as in human prevention and treatment regimens.

In at least some examples, a N,N'-2,5-DKP of the present disclosure may be produced from an α-peptoid (having a generic monomer as illustrated above). In at least some examples, a N,N'-2,5-DKP of the present disclosure may be produced from a β-peptoid. The following structure represents a generic monomer of a β-peptoid backbone:

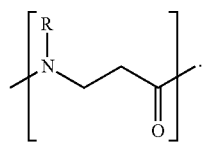

In at least some examples, a N,N'-2,5-DKP may be produced from a hybrid system including at least one α-peptoid and at least one β-peptoid. One skilled in the art will appreciate that achievable ring sizes and conformations may depend on the α-peptoid(s) and/or β-peptoid(s) used.

Methodology for Controlling Cyclization of Peptoids to Form Chiral DKPs

Figure 2:
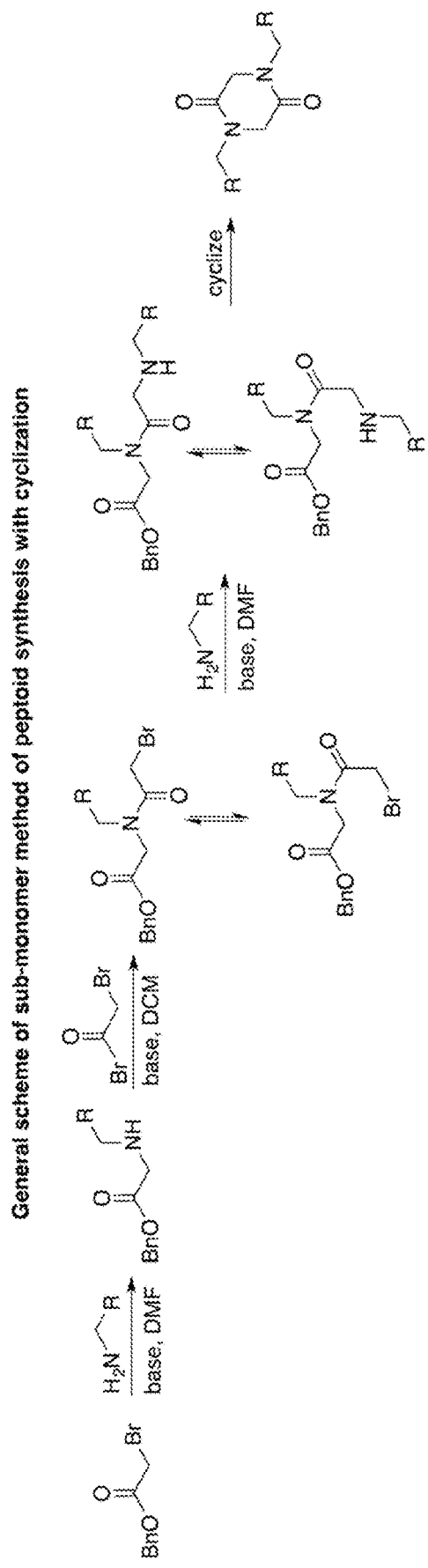
FIG. 2 illustrates a general synthetic scheme of a modified solution phase sub-monomer method of peptoid synthesis, in accordance with embodiments of the present disclosure.

Aspects of the present disclosure relate to methodology for controlling cyclization of peptoids to form chiral DKPs. One benefit of the teachings herein is the synthesis of small peptoids on a large scale for modular assembly into larger peptoids that fold in a predictable manner. A modified sub-monomer method for peptoid synthesis (as illustrated in FIG. 2) may be used in at least some examples. One skilled in the art will appreciate that scope of peptoid synthesis of the present disclosure is not limited to the exact reagents, intermediates, and products illustrated in FIG. 2. One skilled in the art may use teachings disclosed herein, and knowledge in the art, to alter the synthesis scheme of FIG. 2 without deviating from the scope of the present disclosure.

In at least some examples, an ester terminus may be employed instead of an amide terminus. This modification may enable further synthetic modification of either end of a peptoid.

First Reaction

In at least some examples, a first reaction (e.g., a halide displacement reaction) may include reacting a haloacetate ester with an amine to produce a first product having two electrophiles. This first reaction may result in the amine displacing the halide of the haloacetate ester. For example, if the haloacetate ester is reacted with a primary amine, the primary amine may displace the halide in the haloacetate ester to form a secondary amine.

The halide, in the haloacetate ester, may be any halide. In at least some examples, bromine, iodine, or chlorine may be preferred. For example, bromine may be preferred since iodine may require double addition of a primary amine, and since reaction with chlorine is slower than reaction with bromine, in at least some examples. "Double addition" may refer to double the weight or volume of a primary amine being used.

In at least some examples, the ester group of the haloacetate ester (and more particularly the single-bonded oxygen of the ester group) may be bound to one or more aliphatic or aromatic groups. As used herein, an "aliphatic group" is an organic compound in which carbon atoms form open chains (e.g., in the form of alkanes, alkenes, or alkynes), not ring structures. Example aliphatic groups that may be bound to the single-bonded oxygen of the ester group, of a haloacetate ester, include, but are not limited to, methyl, ethyl, propyl, butyl, tert-butyl, or some other group having n number of carbon atoms.

As used herein, an "aromatic group" is a chemical compound having one or more planar rings of atoms joined by covalent bonds of two different kinds (e.g., single and double bonds). Example aromatic groups that may be bound to the single-bonded oxygen of the ester group, of a haloacetate ester, include, but are not limited to, benzyl and p-tolyl.

In at least some examples, the haloacetate ester of the first reaction may be substituted with a non-halogenated acetate ester. A non-halogenated acetate ester may include the same groups, atoms, functionality, etc. as described above for a haloacetate ester, except a non-halogenated acetate ester may include at least one non-halogenated leaving group in place of the halogen(s) of a corresponding haloacetate ester. Non-limiting examples of non-halogenated leaving groups that may be used include mesylates and tosylates. As known in the art, a "mesylate" is any salt or ester of methanesulfonic acid ($CH_3SO_3H$). As further known in the art, a "tosylate" is an anion of p-toluenesulfonic acid ($CH_3C_6H_4SO_3^-$).

When a haloacetate ester is reacted with a primary amine, the nitrogen of the primary amine may displace the halide of the haloacetate ester to form a secondary amine. When a non-halogenated acetate ester is reacted with a primary amine, the nitrogen of the primary amine may displace a non-halogenated leaving group to form a secondary amine.

Various primary amines may be used. For example, aliphatic, aromatic, alkenyl, or alkynyl amines may be used. As used herein, an "alkenyl amine" refers to an amine having an organic group of atoms comprising at least one carbon-carbon double bond. As used herein, an "alkynyl amine" refers to an amine having an organic group of atoms comprising at least one carbon-carbon triple bond.

In addition, primary acyl amines may be used. As used herein, an "acyl amine" refers to an amine having an organic group of atoms with the chemical formula —C(O)R, where R is an alkyl group.

In addition, amines comprising esters, alcohols, and thiols may be used.

The functional group of a primary amine may be protected so the primary amine nitrogen is the only reactive nucleophile (i.e., a chemical species that donates an electron pair to form a chemical bond in relation to a reaction). For example, carboxylic acids may be protected as esters. For further example, diamines may be mono-protected with tert-butoxyl ester (BOC), benzyloxy carbamate (CBz), or the like. For further example, alcohols may be protected as silyl ethers or pivoloyl esters (Piv).

Primary amines that can be used include both achiral and chiral amines. Moreover, dopamine and fluorinated aromatic amines may be used.

There are 1000's of commercially available amines, and various non-commercially, synthetically prepared amines. The first reaction is not limited to the foregoing described amines but, rather, may be performed using the foregoing described amines as well as other commercially and non-commercially available amines.

As described above, the first reaction may produce a first product having two electrophiles. As known in the art, an "electrophile" is a chemical species that accepts an electron pair to form a chemical bond with a nucleophile.

In at least some examples, the haloacetate ester (or non-halogentated acetate ester) may be added to a solution comprising a primary amine and a tertiary amine. Various tertiary amines may be used, such as triethylamine, imidazole, diisopropylethylamine, diazabicyclo[2.2.2]octane (DABCO), or any other tertiary amine.

Displacement (of the halide or non-halogentated functional group) may occur rapidly. For example, displacement may occur as soon as the haloacetate ester (or non-halogentated acetate ester) is added to the solution comprising the primary amine and the tertiary amine.

The function of the tertiary amine may be two-fold. First, the tertiary amine may deprotonate ammonium that is formed upon halide displacement. Second, the tertiary amine may convert any amine hydrochloride salts to corresponding primary amines before displacement takes place. The tertiary amine thus may enable use of hydrochloride salts of any amine to make the amine a nucleophile in situ.

The reaction mixture, of the first reaction, may comprise various solvents. Optimal yield of the first product may be provided when using N,N'-dimethylformamide (DMF) as a solvent. However, one skilled in the art will appreciate that other solvents may be used. For example, halide displacement may be performed using acetonitrile or THF (tetrahydrofuran) as a solvent. Nonetheless, it is noted that yield of the first product may significantly decrease when THF is used as a solvent. Double addition (e.g., by weight or volume) of a primary amine may be used when acetonitrile is used as the solvent.

The first reaction may be performed at various temperatures. In at least some examples, the reaction mixture of the first reaction may be chilled to or about 0° C., or some other temperature below room temperature. In at least some examples, the reaction can be performed up to 90° C., though yields may drop at elevated temperatures for the first reaction. According to at least some example, yields of the first reaction may not change from about 0° C. up through about 50° C., though 0° C. may give the best results in terms of yield and minimizing side products.

The first reaction may be performed for various durations. As a non-limiting example, the first reaction may be performed for as little as 2 hours and as long as 24 hours. In at least some examples, the first reaction may be performed for at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, or at least 23 hours, or minimal durations therebetween (e.g., at least 2.5 hours, at least 3.25 hours, etc.). Duration of the first reaction may be dependent on the steric bulk of the nucleophile and the availability of the haloacetate.

As an illustrative, non-limiting example, to a stirred solution of amine (1 equiv.) and trimethylamine (2 equiv.) in DMF at 0° C. may be added a solution of haloacetate (0.9 equiv.) in DMF. After about 15 minutes, the reaction may be brought to room temperature. The reaction may be followed by thin layer chromatograph (TCL; 4:1 hexanes/ethyl acetate). The reaction time may vary between 3 and 6 hours depending on reagents. Following complete halide displacement, the reaction mixture may be diluted with ethyl acetate and then washed three times with water. The organic layer may be dried with brine, then further dried using sodium sulfate. Upon vacuum filtration, the solvent may be removed in vacuo, producing the first product. The first product may be purified using Snap Ultra silica column on Biotage I solera Four system with 4:1 hexanes/ethyl acetate isocratic method with UV detection.

Illustrative, non-limiting examples of products of the first reaction include:

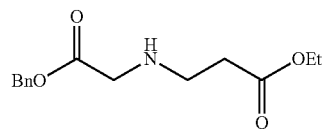 [SMILES: CCOC(=O)CCNCC(=O)OCc1ccccc1]

ethyl 3-((2-(benzyloxy)-2-oxoethyl)amino)propanoate;

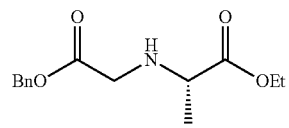 [SMILES: CCOC(=O)[C@H](C)NCC(=O)OCc1ccccc1]

ethyl (2-(benzyloxy)-2-oxoethyl)-L-alaninate;

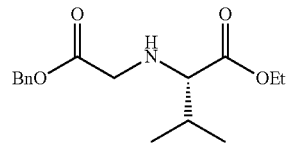 [SMILES: CCOC(=O)[C@@H](NCC(=O)OCc1ccccc1)C(C)C]

ethyl (2-(benzyloxy)-2-oxoethyl)-L-valinate;

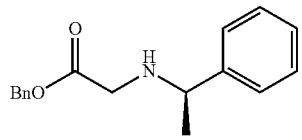 [SMILES: C[C@@H](NCC(=O)OCc1ccccc1)c1ccccc1]

benzyl (S)-(1-phenylethyl)glycinate;

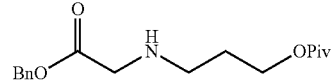

3-((2-(benzyloxy)-2-oxoethyl)amino)propyl pivalate;

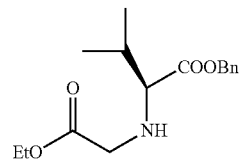

benzyl N-2-(2-bromoacetyl)-N-(2-((4-methylbenzyl)oxy)-2-oxoethyl)-L-alaninate;

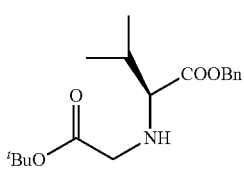

benzyl (2-(tert-butoxy)-2-oxoethyl)-L-valinate;

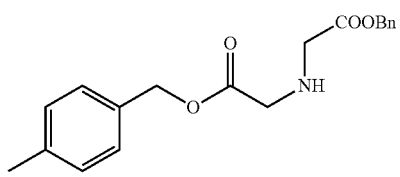

benzyl (2-((4-methylbenzyl)oxy)-2-oxoethyl)glycinate;

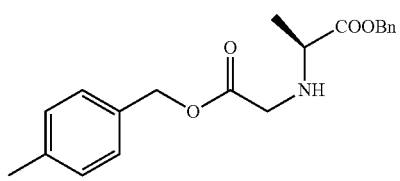

benzyl (2-((4-methylbenzyl)oxy)-2-oxoethyl)-L-alaninate;

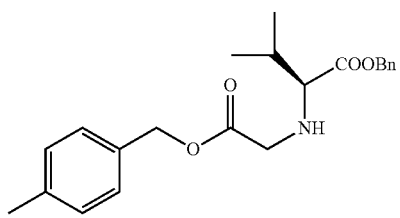

benzyl (2-((4-methylbenzyl)oxy)-2-oxoethyl)-L-valinate; and

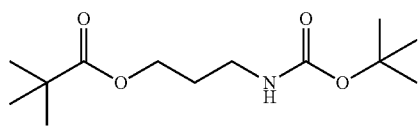 [SMILES: CC(C)(C)OC(=O)NCCCOC(=O)C(C)(C)C]

3-((tert-butoxycarbonyl)amino)propyl pivalate.

Second Reaction

A second reaction (e.g., haloacetylation) may be performed using the first product. For example, haloacetylation of the secondary amine produced in the first reaction may occur upon adding the first product to a solution comprising haloacetyl halide. In at least some examples, the solution may comprise haloacetyl halide and pyridine (or any tertiary amine such as, but not limited to, triethylamine, diisopropylethylamine, or other amine).

The haloacetyl halide may comprise one or more halides. When the haloacetyl halide comprises two or more halides, all of the halides may be the same, or the haloacetyl halide may comprise at least two different halides. In at least some examples, bromine may be preferred. Example haloacetyl halides include, but are not limited to bromoacetyl bromide (illustrated in FIG. 2), chloroacetyl chloride, chloroacetyal bromide, etc.

When the haloacetyl halide comprises an acid halide and an aliphatic halide, the secondary amine (created in the first reaction) may exclusively react with the acid halide, and not an aliphatic halide.

The N-hydroxysuccinimide (NHS)-ester of a haloacetic acid may also be used as a reagent.

In at least some examples, the solution, comprising the haloacetyl halide, may further comprise at least one base. A non-limiting list of bases that may be used includes tertiary and aromatic amines such as, but not limited to, triethylamine, diisopropylethylamine, pyridine, imidazole, pyrazine, and trimethylamine. The R groups attached to the nitrogen of the amine of a base may be aromatic or aliphatic.

The solution, comprising the haloacetyl halide (and optionally a base(s)) may have various solvents. In at least some examples, dichloromethane (DCM), acetonitrile, THF, and/or DMF may be used as a solvent.

As an example, a solution, comprising haloacetyal halide, a base(s), and DCM as a solvent, may produce a charged intermediate that stirs as a colored (e.g., yellow) slurry. The first product may be added to this slurry. In at least some examples, the slurry may be chilled to or about 0° C. prior to addition of the first product. Addition of the first product to the slurry may result in the secondary amine (of the first product) becoming fully haloacetylated. In at least some examples, full haloacetylation of the secondary amine (of the first product) may occur in less than about 2 hours. Haloacetylation of the secondary amine (of the first product) may be visually represented by the color of the stirring slurry dissipating, with full haloacetylation being visually represented by disappearance of the slurry's color. A result of full haloacetylation may yield a complete solution of dissolved "second product."

The product of the second reaction, in at least some examples, may appear as a mixture of two configurations in $^1$H NMR due to the presence of two amide rotamers in equal distribution.

As an illustrative, non-limiting example, haloacetyl halide (1 equiv.) may be added to a solution of DCM at 0° C. Pyridine (1.1 equiv.) may be slowly added via syringe, forming a suspension. Separate, the first product may be diluted with DCM via pipette. The formed suspension may be added to the diluted first product (1 equiv.). The reaction may be brought to room temperature by removal of ice bath after about 30 minutes. The reaction may be followed by TLC (4:1 hexanes/ethyl acetate). The reaction may be finished in about 45-90 minutes. Upon reaction completion, the reaction mixture may be washed with saturated citric acid solution, water, brine, and then further dried with sodium sulfate. Upon vacuum filtration, the DCM may be removed in vacuo, producing the second product. The second product may then be purified using Snap Ultra silica column on Biotage Isolera Four system with gradient from 20% ethyl acetate in hexanes to 80% ethyl acetate in hexanes.

Illustrative, non-limiting examples of products of the second reaction include:

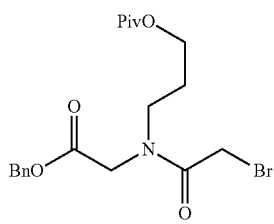

3-(N-(2-(benzyloxy)-2-oxoethyl)-2-bromoacetamido)propyl pivalate;

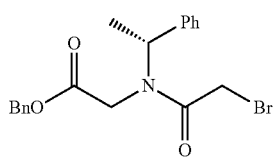

benzyl (R)—N-(2-bromoacetyl)-N-(1-phenylethyl)glycinate;

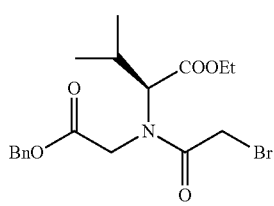 [SMILES: CCOC(=O)[C@H](C(C)C)N(CC(=O)OCc1ccccc1)C(=O)CBr]

ethyl N-(2-(benzyloxy)-2-oxoethyl)-N-(2-bromoacetyl)-L-valinate;

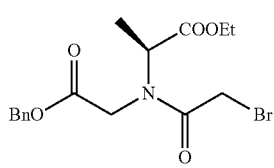 [SMILES: CCOC(=O)[C@H](C)N(CC(=O)OCc1ccccc1)C(=O)CBr]

ethyl N-(2-(benzyloxy)-2-oxoethyl)-N-(2-bromoacetyl)-L-alaninate;

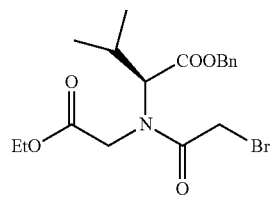

benzyl N-(2-bromoacetyl)-N-(2-ethoxy-2-oxoethyl)-L-valinate;

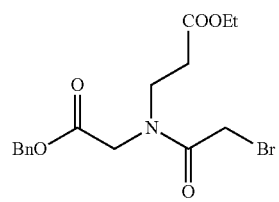 [SMILES: CCOC(=O)CCN(CC(=O)OCc1ccccc1)C(=O)CBr]

ethyl 3-(N-(2-(benzyloxy)-2-oxoethyl)-2-bromoacetamido)propanoate;

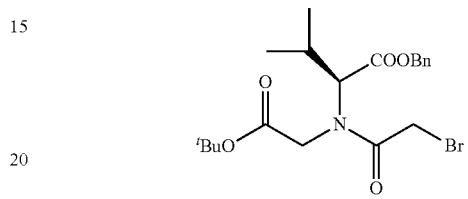

benzyl N-(2-bromoacetyl)-N-(2-(tert-butoxy)-2-oxoethyl)-L-valinate;

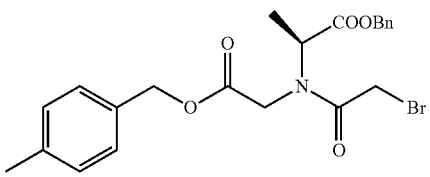

benzyl N-(2-bromoacetyl)-N-(2-(4-methylbenzyl)oxy)-2-oxoethyl)-L-alaninate;

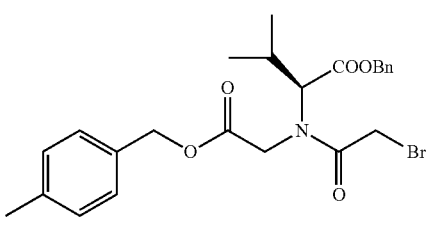

benzyl N-(2-bromoacetyl)-N-(2-(4-methylbenzyl)oxy)-2-oxoethyl)-L-valinate; and

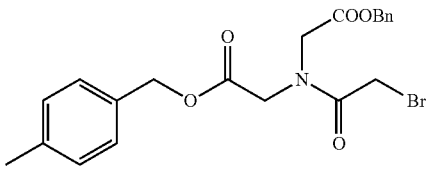

benzyl N-(2-bromoacetyl)-N-(2-((4-methylbenzyl)oxy)-2-oxoethyl)glycinate.

Third Reaction

A third reaction (including the same or similar parameters as the above described halide displacement reaction) may then be repeated with the product of the second reaction. Here, another primary amine may be added to the haloacetate of the second product, to produce a peptoid dimer.

N,N'-2,5-DKP Formation

Once a peptoid dimer is formed, it may cyclize spontaneously. Upon cyclization the original ester of the haloacetate may be eliminated. Depending on the identity of the amine side chains, such as bulky, aliphatic, or aromatic groups, heat may be applied to complete the cyclization.

In an illustrative, non-limiting example, to a stirred solution of amine (1 equiv.) and trimethylamine (2 equiv.) in DMF at 0° C. may be added a solution of peptoid dimer (0.9 equiv.) in DMF. After about 30 minutes, the reaction mixture may be brought to room temperature. The reaction may be followed by TLC (4:1 hexanes/ethyl acetate). Depending on the amine sequence, complete cyclization may range from about 4 hours to about 48 hours. Following complete conversion, the reaction mixture may be diluted with ethyl acetate and then washed three times with water. The organic layer may be dried with sodium sulfate and then, upon vacuum filtration, may be removed in vacuo, producing N,N'-2,5'DKP. The N,N'-2,5-DKP may be purified using Snap Ultra silica column on Biotage Isolera Four system with stepwise gradient method with UV detection.

The following are illustrative, non-limiting examples of N,N'-2,5-DKPs that were synthesized using the foregoing methodology:

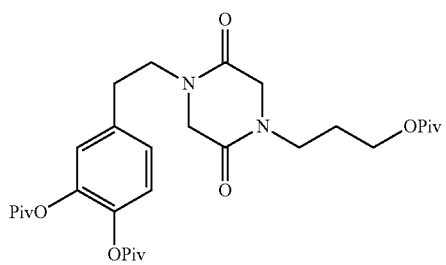

4-(2-(2,5-dioxo-4-β-(pivaloyloxy)propyl)piperazin-1-yl) ethyl)-1,2-phenylene-bis(2,2-dimethylpropanoate);

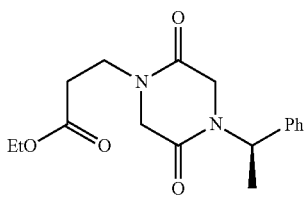 [SMILES: CCOC(=O)CCN1CC(=O)N([C@H](C)c2ccccc2)CC1=O]

ethyl (R)-3-(2,5-dioxo-4-(1-phenylethyl)piperazin-1-yl)proponate;

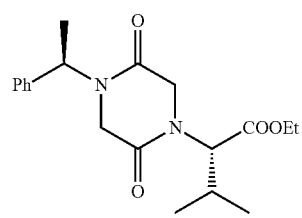

ethyl (S)-2-(2,5-dioxo-4-((R)-1-phenylethyl)piperazin-1-yl)-3-methylbutanoate;

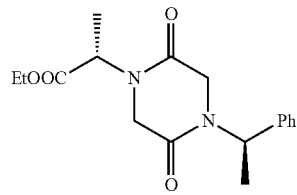 [SMILES: CCOC(=O)[C@H](C)N1CC(=O)N([C@H](C)c2ccccc2)CC1=O]

ethyl (S)-2-(2,5-dioxo-4-((R)-1-phenylethyl)piperazin-1-yl)proponate;

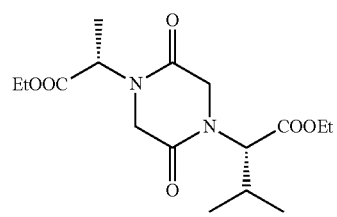 [SMILES: CCOC(=O)[C@H](C(C)C)N1CC(=O)N([C@@H](C)C(=O)OCC)CC1=O]

ethyl (S)-2-(4-((S)-1-ethyoxy-1-oxopropan-2-yl)-2,5-dioxopiperazin-1-yl)-3-methylbutanoate;

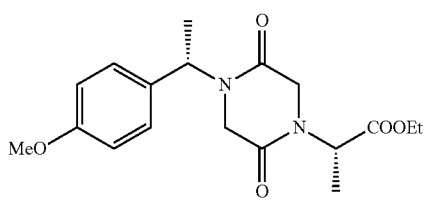 [SMILES: CCOC(=O)[C@H](C)N1CC(=O)N([C@@H](C)c2ccc(OC)cc2)CC1=O]

ethyl (S)-2-(4-((S)-1-(4-methyoxyphenyl)ethyl)-2,5-dioxopiperazin-1-yl)propanoate;

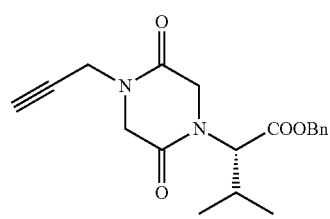

benzyl (S)-2-(2,5-dioxo-4-(prop-2-yn-1-yl)piperazin-1-yl)-3-methylbutanoate;

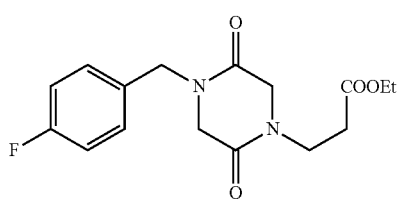 [SMILES: CCOC(=O)CCN1CC(=O)N(Cc2ccc(F)cc2)CC1=O]

ethyl 3-(4-(4-fluorobenzyl)-2,5-dioxopiperazin-1-yl)propanoate;

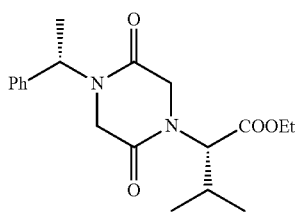 [SMILES: CCOC(=O)[C@H](C(C)C)N1CC(=O)N([C@@H](C)c2ccccc2)CC1=O]

ethyl (S)-2-(2,5-dioxo-4-((S)-1-phenylethyl)piperazin-1-yl)-3-methylbutanoate;

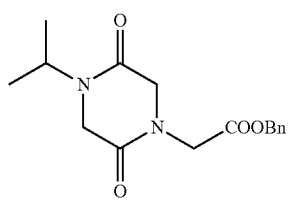

benzyl 2-(4-isopropyl-2,5-dioxopiperazin-1-yl)acetate;

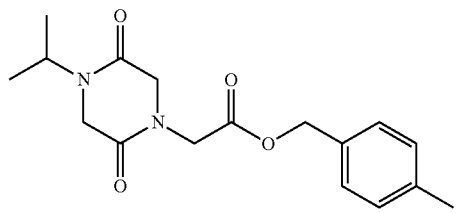 [SMILES: Cc1ccc(COC(=O)CN2CC(=O)N(C(C)C)CC2=O)cc1]

4-methylbenzyl 2-(4-isopropyl-2,5-dioxopiperazin-1-yl)acetate;

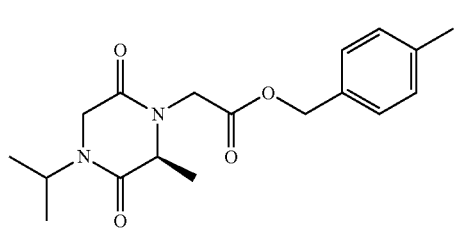 [SMILES: Cc1ccc(COC(=O)CN2C(=O)CN(C(C)C)C(=O)[C@@H]2C)cc1]

4-methylbenzyl (S)-2-(4-isopropyl-2-methyl-3,6-dioxopiperazin-1-yl)acetate;

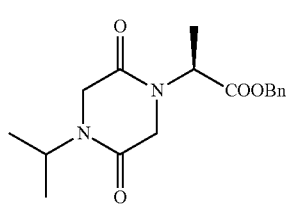

benzyl (S)-2-(4-isopropyl-2,5-dioxopiperazin-1-yl)propanoate;

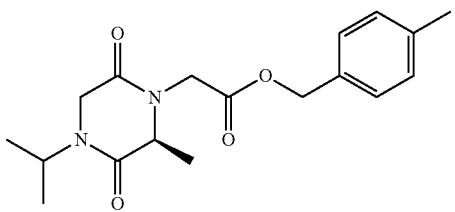 [SMILES: Cc1ccc(COC(=O)CN2C(=O)CN(C(C)C)C(=O)[C@@H]2C)cc1]

4-methylbenzyl (S)-2-(4-isopropyl-2-methyl-3,6-dioxopiperazin-1-yl)acetate;

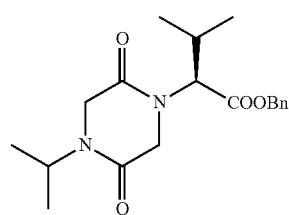

benzyl (S)-2-(4-isopropyl-2,5-dioxopiperazin-1-yl)-3-methylbutanoate;

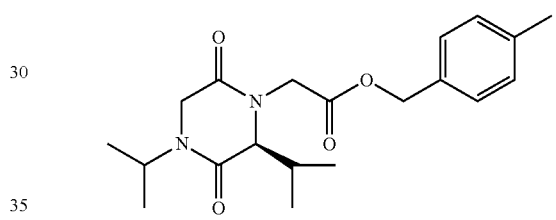

4-methylbenzyl (S)-2-(2,4-diisopropyl-3,6-dioxopiperazin-1-yl)acetate;

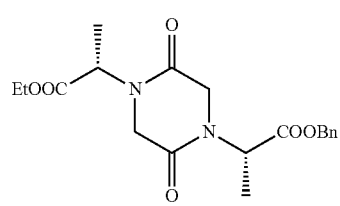

benzyl (S)-2-(4-((S)-1-ethoxy-1-oxopropan-2-yl)-2,5-dioxopiperazin-1-yl)propanoate; and

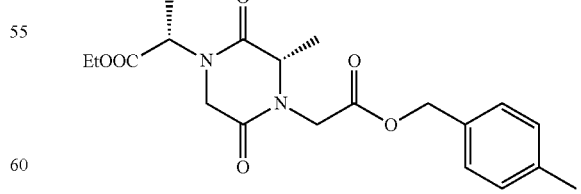

ethyl (S)-2-((S)-3-methyl-4-(2-((4-methylbenzyl)oxy)-2-oxoethyl)-2,5-dioxopiperazin-1-yl)propanoate.

Figure 3:
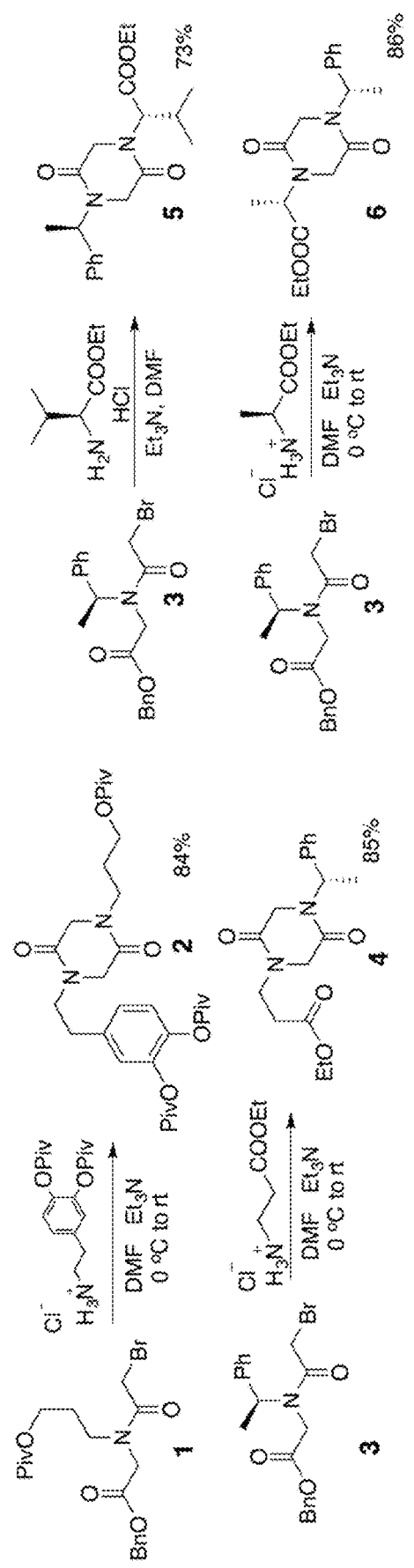
FIG. 3 illustrates example haloacetylation reaction products, and reaction reagents and conditions to produce specific N,N'-2,5-DKPs, in accordance with embodiments of the present disclosure.
Figure 4:
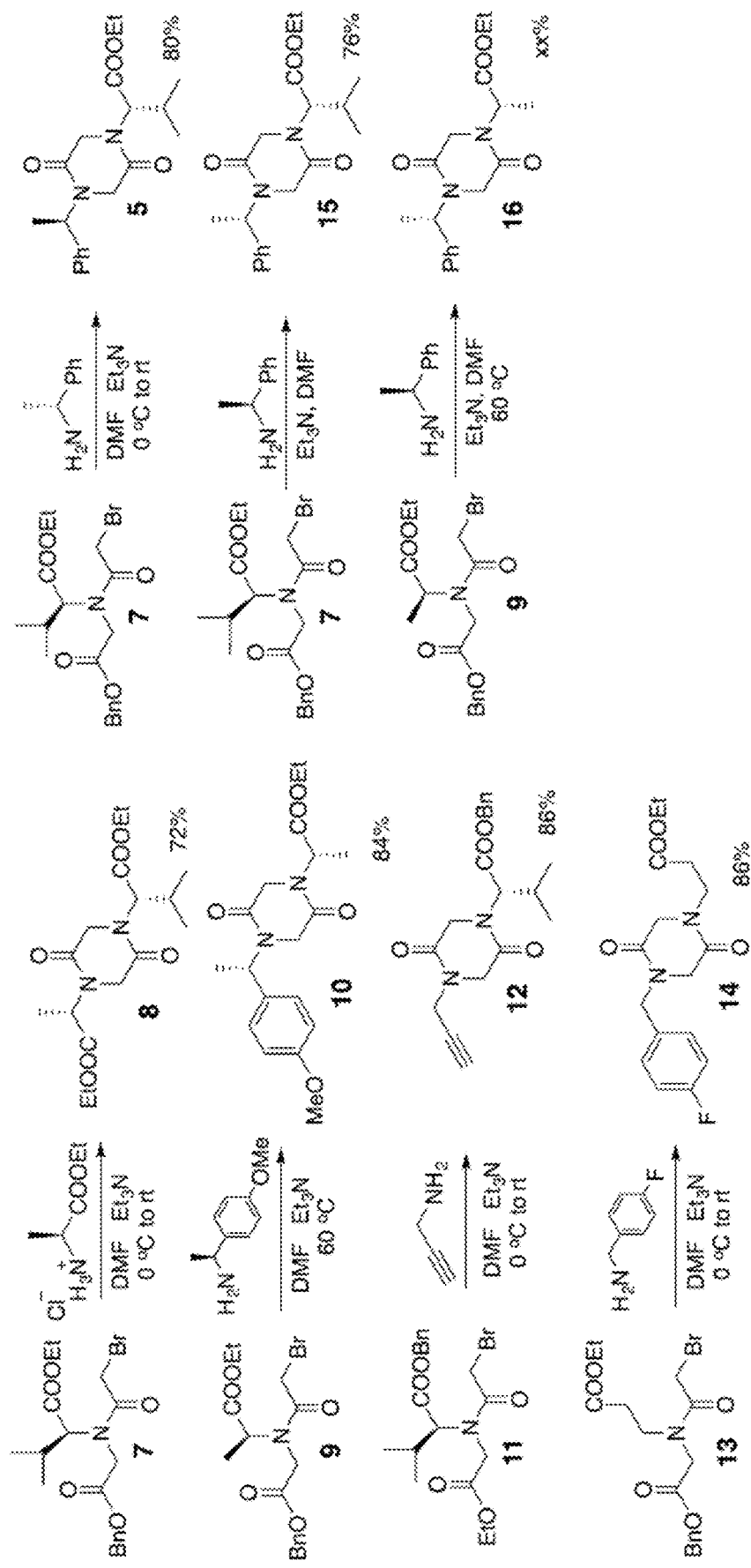
FIG. 4 illustrates example haloacetylation reaction products, and reaction reagents and conditions to produce specific N,N'-2,5-DKPs, in accordance with embodiments of the present disclosure.

FIGS. 3 and 4 illustrate specific, non-limiting examples of haloacetylation reaction products, and reaction reagents and conditions to produce specific N,N'-2,5-DKPs.

Purification of First Product

In at least some examples, the first product may be purified. Various purification techniques may be used. In at least some examples, the first product may be purified under standard chromatography techniques.

Purification of Second Product

In at least some examples, the second product may be purified. Various purification techniques may be used. In at least some examples, the second product may be purified under standard chromatography techniques.

Purification of N,N'-2,5-DKP

In at least some examples, the resulting N,N'-2,5-DKP may be purified. Various purification techniques may be used. In at least some examples, the N,N'-2,5-DKP may be purified under standard chromatography techniques.

Administration of N,N'-2,5-DKPs

In connection with the treatment of various diseases in vivo, N,N'-2,5-DKPs of the present disclosure may be introduced systemically to a patient having, or suspected of having, cancer, pneumonia, diabetes, etc. N,N'-2,5-DKPs of the present disclosure may preferably be introduced systemically, although localized administration may be appropriate in some circumstances (e.g., in the case of localized tumors or targeted delivery of therapeutics to the lungs or liver). N,N'-2,5-DKPs of the present disclosure may be formulated for oral, topical, or rectal administration using well-known formulation methodologies. Additionally, when formulated in a physiologically acceptable buffer solution, N,N'-2,5-DKPs of the present disclosure may be introduced parenterally (e.g., non-orally but intravenously or by injection). The determination of effective therapeutic levels, and the formulations required to deliver such effective therapeutic levels, are determined on a case-by-case basis which is dependent, for example, on the extent of the disease (e.g., cancer, pneumonia, or diabetes) being treated. Such determinations are readily made by one skilled in the art using no more than routine experimentation.

Rotameric Equilibrium

Figure 5:
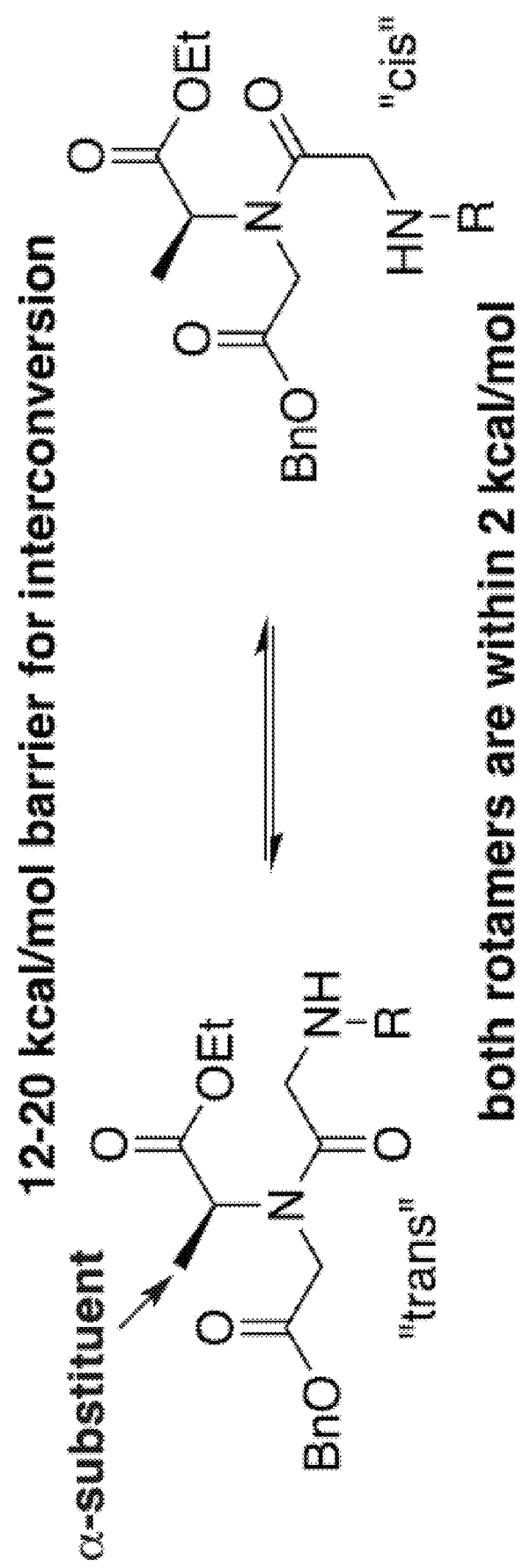
FIG. 5 illustrates how amide rotamers are close in energy, but have a high barrier of switch from one to another, in accordance with embodiments of the present disclosure.

As illustrated in FIG. 2, a product of a haloacetylation reaction (e.g., the aforementioned second product), and a peptoid dimer (e.g., a product of the aforementioned third reaction), may exist as cis and trans amide rotamers. As illustrated in FIG. 5, amide rotamers are close in energy, but have a high barrier to switch from one to another.

It was found that, when an amino acid ester is employed as the primary amine in the halide displacement reaction, the product of the halide displacement reaction includes two electrophiles. In such situations, a second primary amine (added in the "third" reaction according to the aforementioned methodology) may attack either one of the electrophiles. It was observed, through experimentation, that the second primary amine (a nucleophile) differentiates between the two electrophiles, and attacks a single one.

Figure 6:
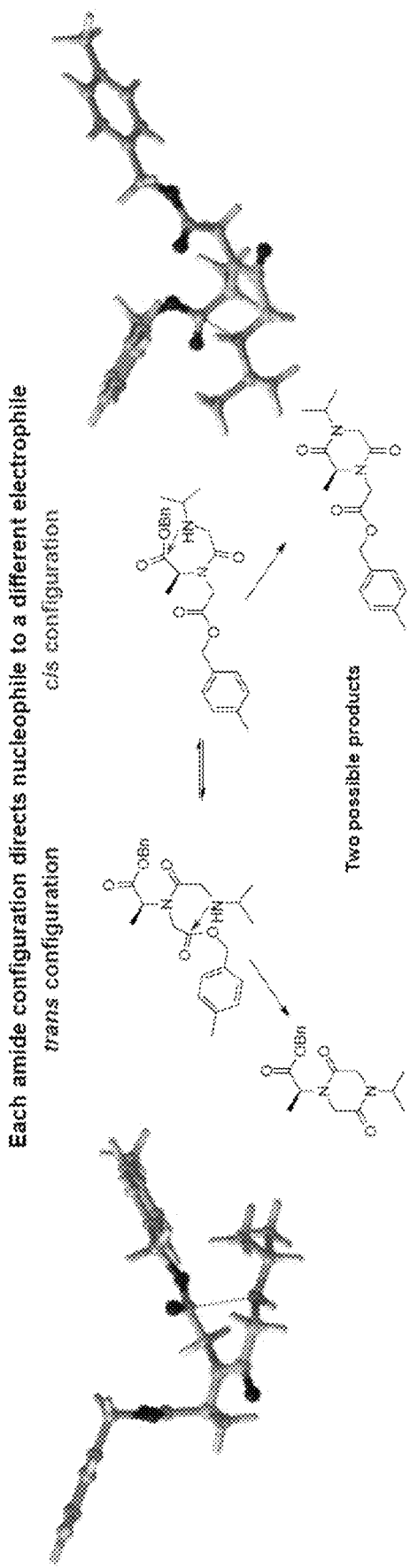
FIG. 6 illustrates that, when two electrophiles are present, both amide configurations may be productive toward separate cyclization reactions, in accordance with embodiments of the present disclosure.

As illustrated in FIG. 6, both amide configurations of a molecule may be productive towards different DKPs. If both amides are in equilibrium, both DKP products would form at equal amounts, assuming that the activation barriers for cyclization were similar in energy.

In at least some examples, reaction temperature, from a kinetic perspective, has a two-fold effect on the overall reaction. For example, first, a change in temperature may change the equilibrium between amide configurations. Second, elevated temperatures may also alter the energetic landscape in terms of increasing the ability of overcoming the activation barrier, thus accelerating the reaction. This acceleration may not be symmetric, meaning not equally distributed between both cyclization products. Reaction temperature, therefore, may or may not change the product distribution between the two possible 2,5-DKP products.

Selective Cyclization

Side Chain Configuration

In at least some examples, the ratio of amide configurations in peptoid dimers may be dependent on the side chain. For example, for large side chains, such as the chiral phenylethyl groups, the cis configuration may dominate in DMF at room temperature. The trans side chain may be more pronounced as the side chain size decreases. As an example, sterics derived from a propyl-derived side chain may cause a higher energy requirement for amide interconversion then a 1-phenylethyl side chain.

Nucleophile Identity

In at least some examples, the identity of the amine nucleophile may impact amide interconversion. In at least some examples, amine nucleophile identity may have a lesser impact on amide interconversion that side chain configuration.

As illustrated in FIG. 3, selectivity and high yields were obtained with a variety of side chains and nucleophiles (i.e., primary amines).

Partial Blockage of Amine Nucleophile Attack

Haloacetamides that are formed in the second reaction may result in equal population of both amide configurations. Due to differential blocking of the alkyl halide by sterics (bulk of the side chains), the amine nucleophile may react preferentially with one amide configuration; thus, forming an unequal population of peptoid dimer amide configurations. This unequal distribution of amide rotamers may influence the selectivity of the cyclization reaction to form 2,5-DKPs.

Examples

Monte Carlo Simulations

Monte Carlo simulations were conducted using the open-source version of the charm simulation package. For each molecule, eight different starting configurations were generated that oriented the nucleophile to the plan described by the central nitrogen and its three bonded neighbors (tertiary amine). The orientation of the nucleophile pointed the carbonyl group of the nucleophile towards the tolyl leaving group (cis) or the benzyl leaving group (trans). The dihedrals orientations for the leaving groups oriented the carbonyl group either above or below this plane, allowing both orientations of the nucleophilic attack to be assessed. After enforcing these configurations, each configuration was minimized with conjugate gradient descent (2000 steps) followed by Newton-Raphson or Stochastic Dynamics (500 steps). All internal angles were held constant, and all torsional angles were permitted to rotate at a maximum of 25° with a move-probability of 0.4. Metropolis Monte Carlo was then run for 10' steps and snapshots were taken every 100 steps.

Figure 7:
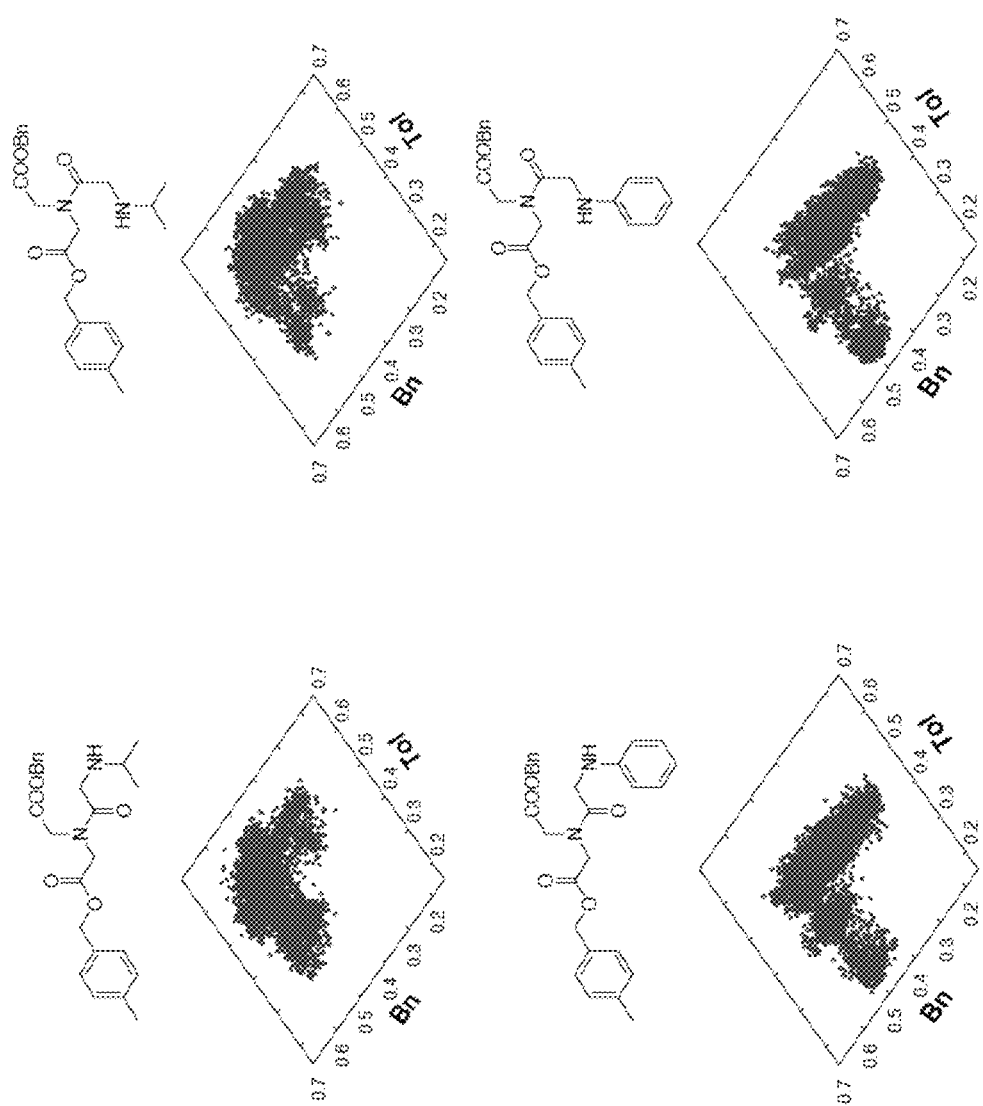
FIG. 7 illustrates Monte Carlo simulations for a hydrogen α-substituent and at 25° C., in accordance with embodiments of the present disclosure.

FIG. 7 illustrates Monte Carlo simulations for a hydrogen α-substituent and at 25° C. As illustrated, there is no selectivity when isopropylamine is the nucleophile. Both configurations of amide rotamers projected nearly an equal number of trajectories towards both esters. Each amide rotamer had similar numbers of trajectories towards both ester electrophiles. When the nucleophile was switched to phenylamine, a mild selectivity towards the tolyl ester was predicted. This suggests that the identity of the nucleophile can have an effect on the selectivity of cyclization.

Figure 8:
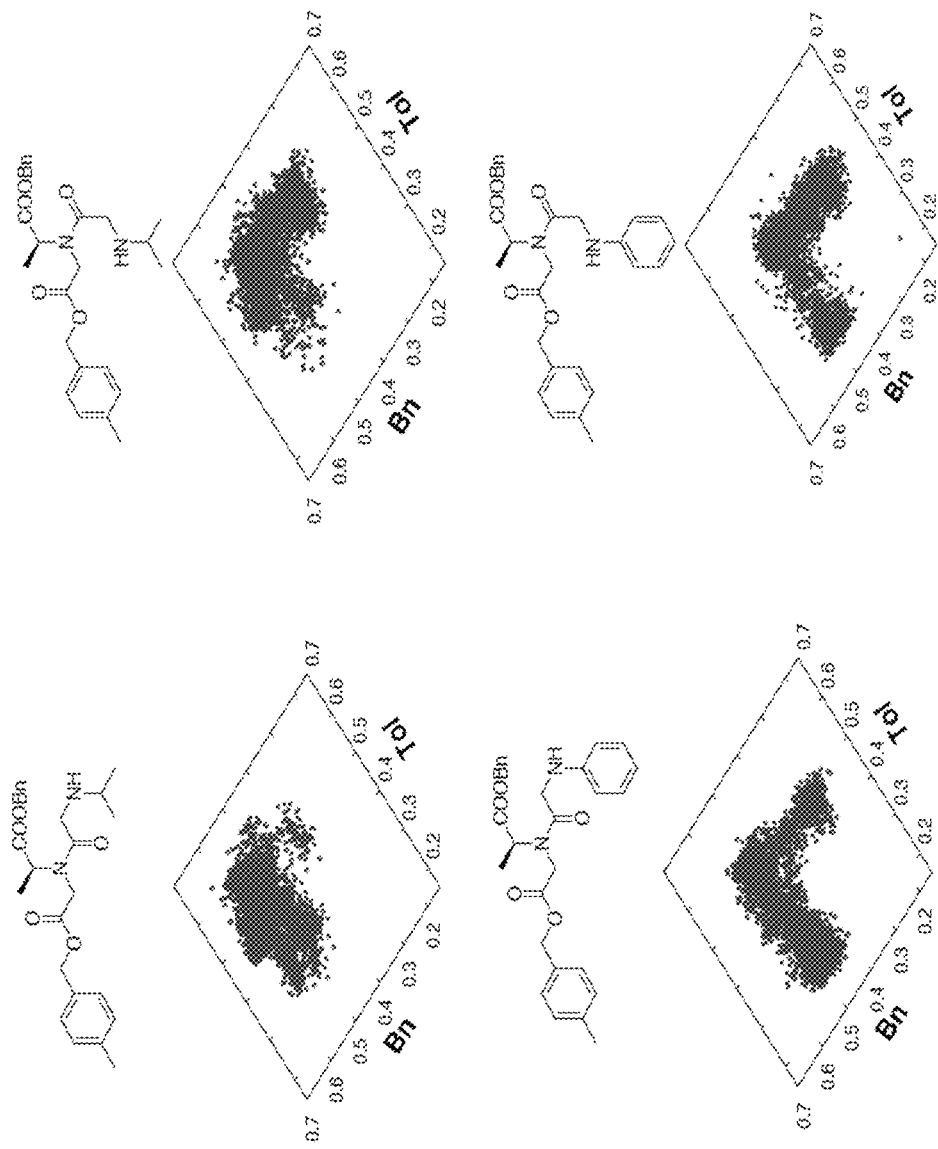
FIG. 8 illustrates Monte Carlo simulations for a methyl α-substituent and at 25° C., in accordance with embodiments of the present disclosure.

FIG. 8 illustrates Monte Carlo simulations for a methyl α-substituent and at 25° C. Simulations favored modest selectivity based on which amide rotamer is present. The trans configuration had an increased number of trajectories towards the tolyl ester. Conversely, the cis configuration favored trajectories towards the benzyl ester. The degree of selectivity was enhanced when the nucleophile was changed to phenylamine. Selectivity of this cyclization will be based on which configuration of the amide rotamer is more prevalent in solution, which could be controlled by temperature.

Figure 9:
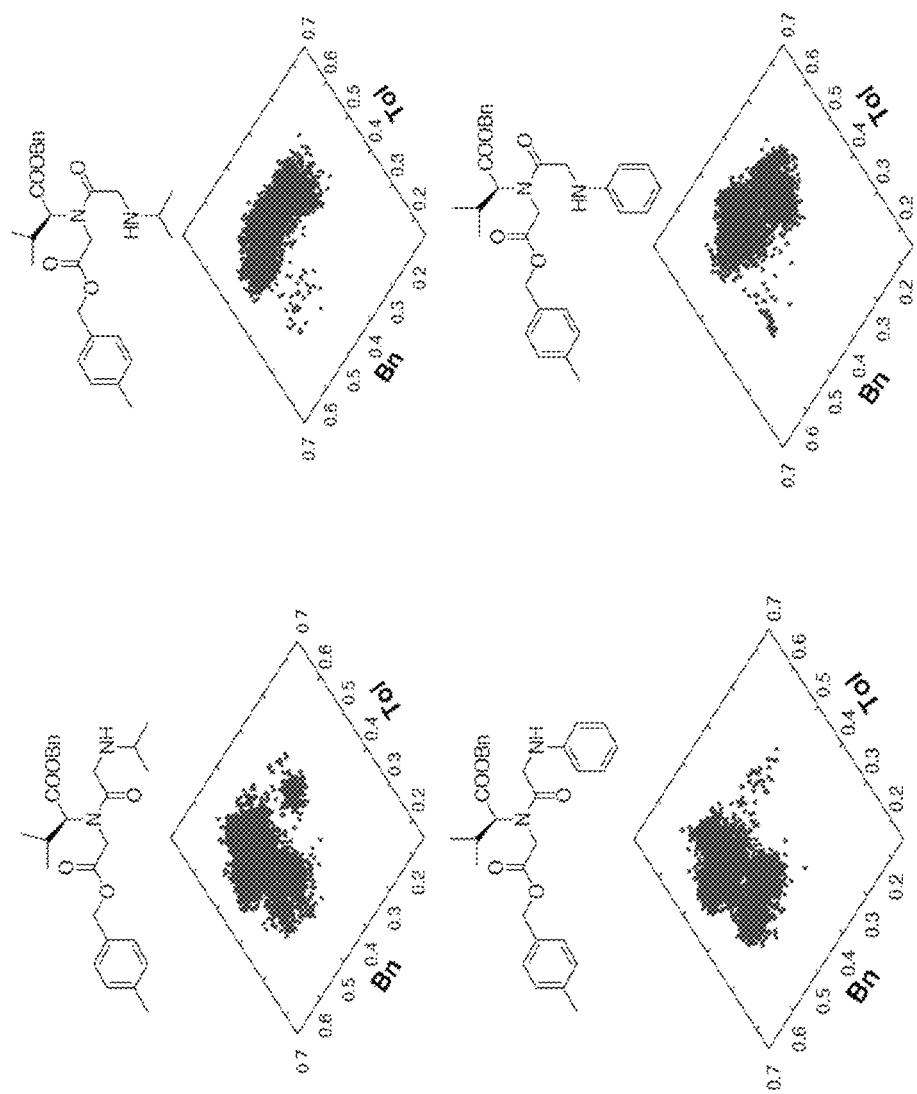
FIG. 9 illustrates Monte Carlo simulations for an isopropyl α-substituent and at 25° C., in accordance with embodiments of the present disclosure.

FIG. 9 illustrates Monte Carlo simulations for an isopropyl α-substituent and at 25° C. Simulations predicted a very high degree of selectivity based on the configuration of the amide rotamer. In this case, changing the nucleophile does not predict a significant change in the selectivity as compared with isopropylamine.

Figure 10:
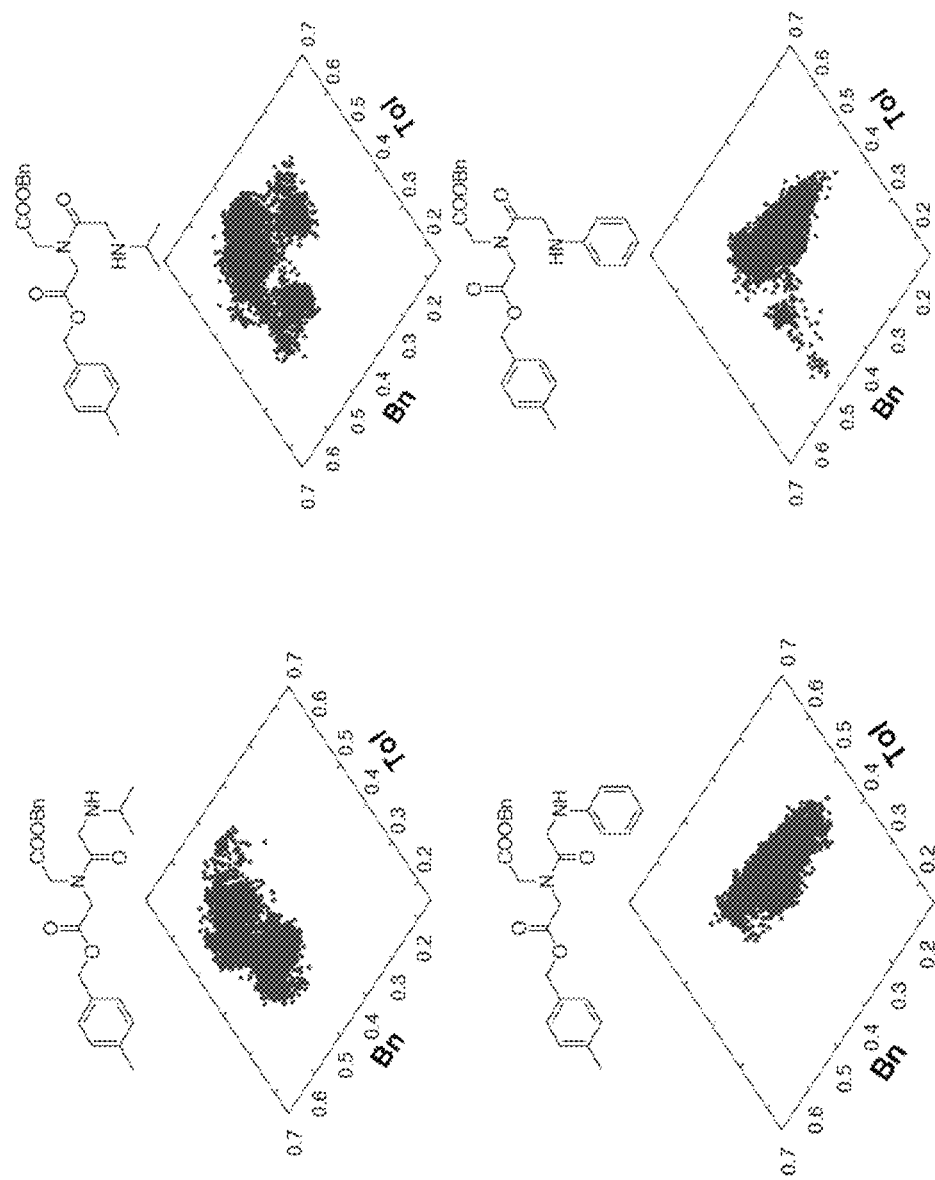
FIG. 10 illustrates Monte Carlo simulations for a hydrogen α-substituent and at 0° C., in accordance with embodiments of the present disclosure.

FIG. 10 illustrates Monte Carlo simulations for a hydrogen α-substituent and at 0° C. Simulations predicted that cooling the reaction to 0° C. would have each amide rotamer prefer to go to a different electrophile. This is not unexpected since the configurations of the amide rotamers would be more rigid.

Figure 11:
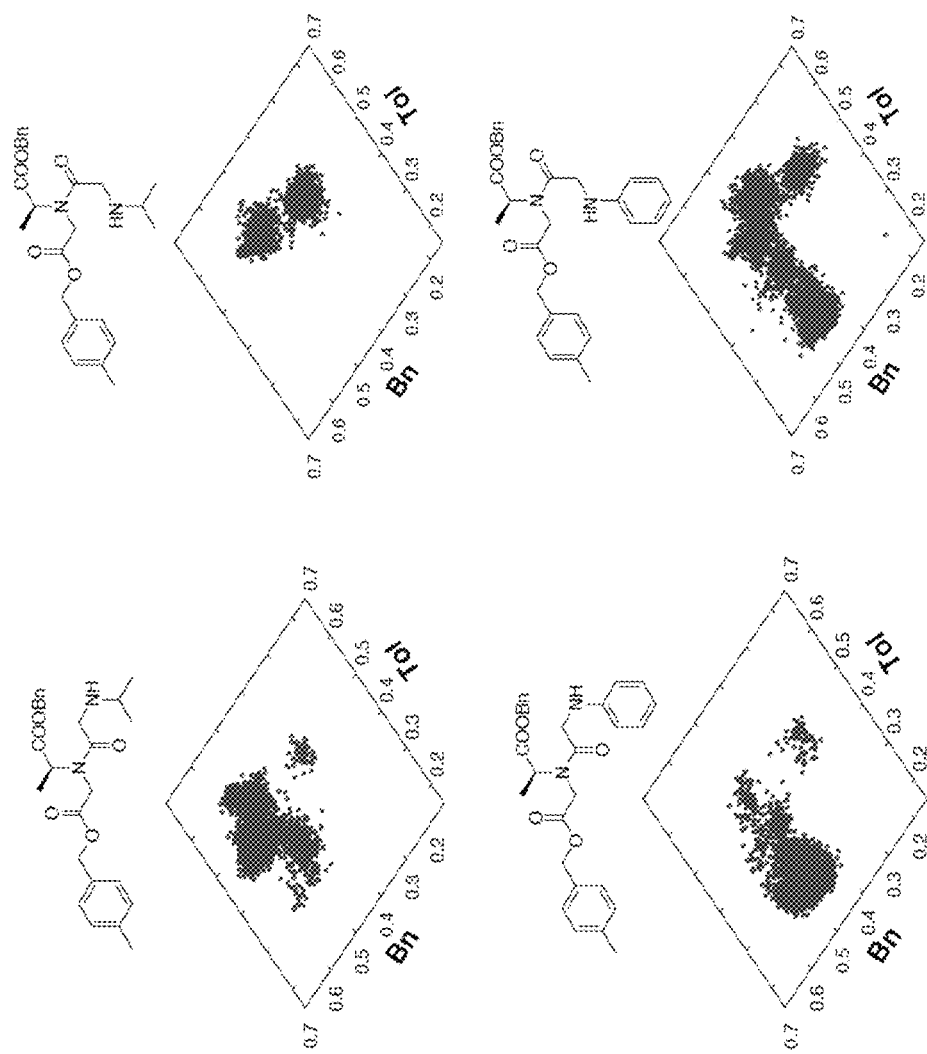
FIG. 11 illustrates Monte Carlo simulations for a methyl α-substituent and at 0° C., in accordance with embodiments of the present disclosure.

FIG. 11 illustrates Monte Carlo simulations for a methyl α-substituent and at 0° C. Simulations predicted that cooling the reaction to 0° C. would have each amide rotamer prefer to go to a different electrophile. This is not unexpected since the configurations of the amide rotamers would be more rigid. When the nucleophile is switched to phenylamine, more trajectories favor the benzyl ester. This implies that the identity of the nucleophile has a significant effect on the selectivity of cyclization.

Figure 12:
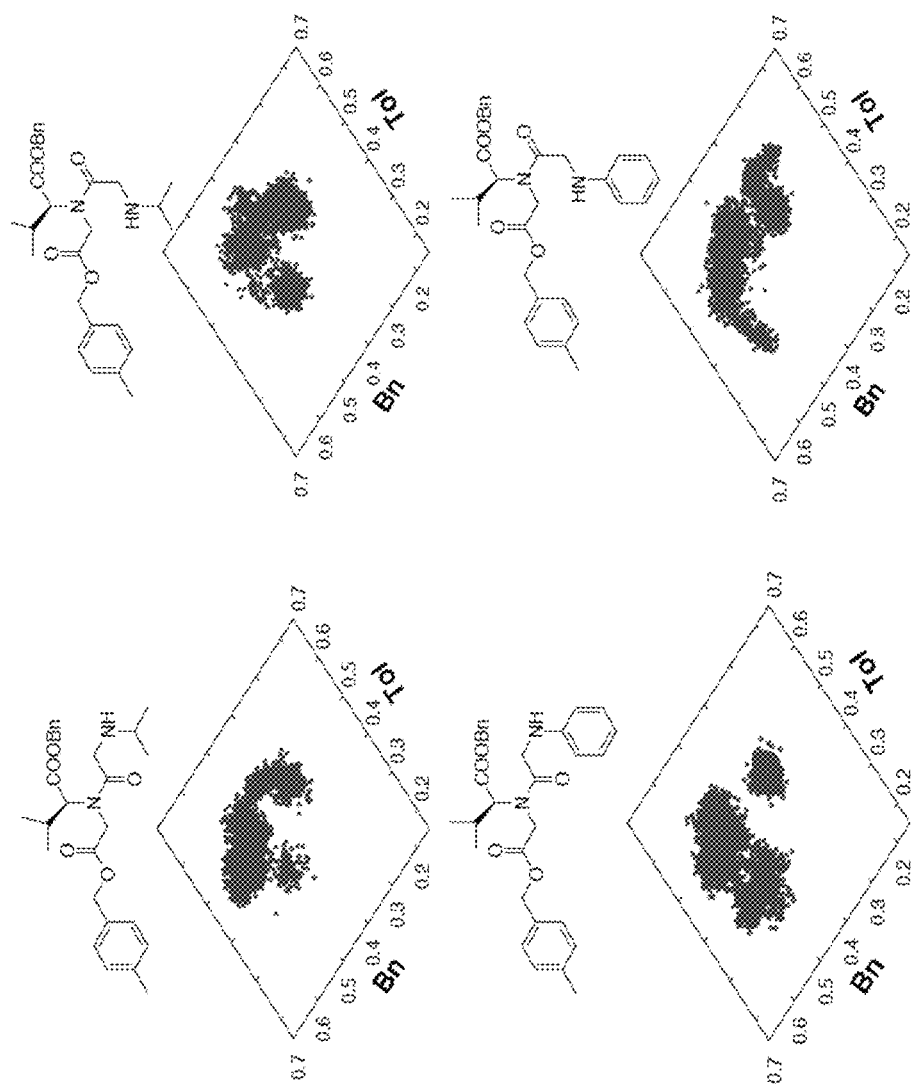
FIG. 12 illustrates Monte Carlo simulations for an isopropyl α-substituent and at 0° C., in accordance with embodiments of the present disclosure.

FIG. 12 illustrates Monte Carlo simulations for an isopropyl α-substituent and at 0° C. There is no preference in trajectories toward either electrophile for both amide configurations at 0° C. The large α-substituent has an equal effect on both sets of trajectories equally. When the nucleophile is switched to phenylamine, a slight trajectory preference is predicted. The trans rotamer has a higher population of trajectories that point towards the benzyl ester. Conversely, the cis rotamer configuration has a higher population of trajectories towards the tolyl ester.

Experiments

Selective cyclizations were achieved through a combination of geometric control and control over amide equilibrium. Identity and size of the amine nucleophile also assisted in directing cyclization. Some cyclizations required heat to obtain full cyclization. The rate of cyclization is the rate-determining step based on experimental observation. Heat not only enabled cyclization, but also altered the equilibrium between rotameric species.

Figure 13:
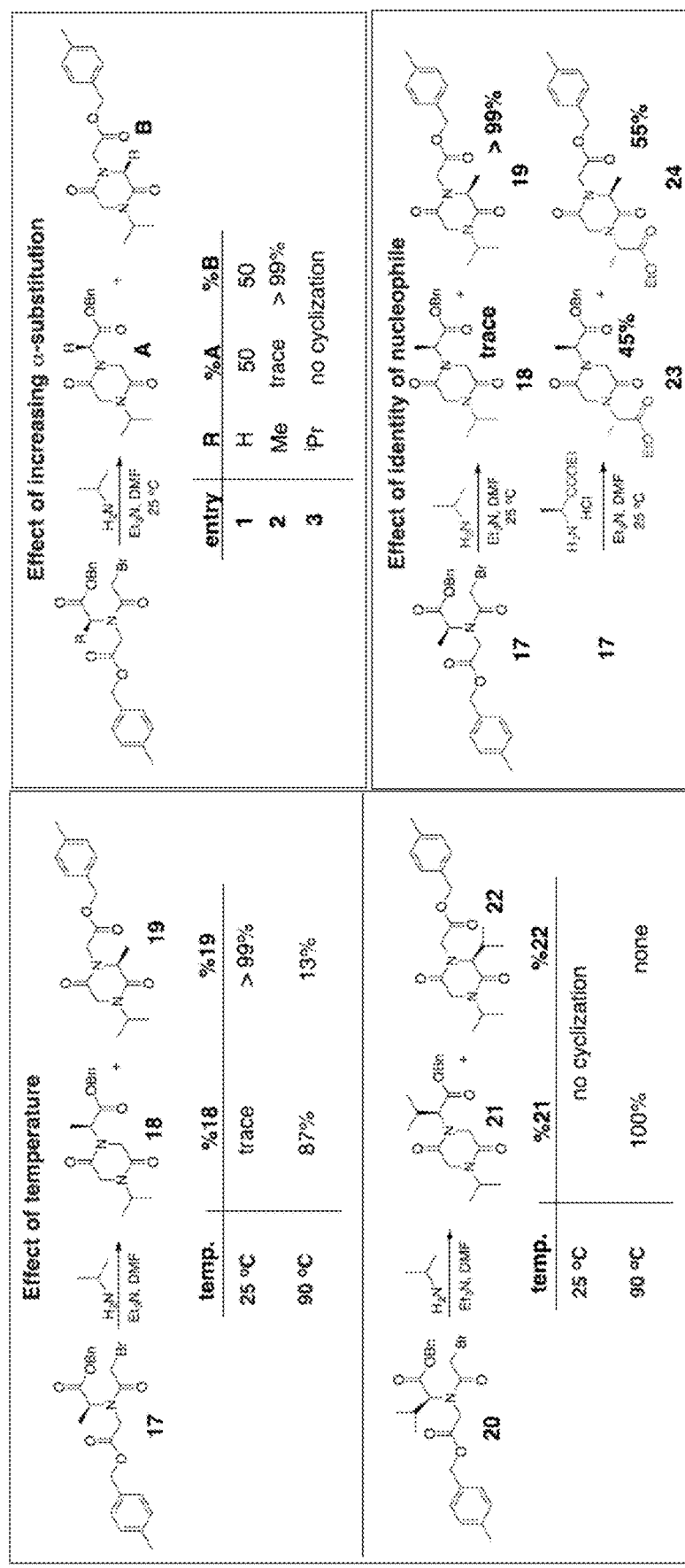
FIG. 13 illustrates a controlled set of experiments to gauge the effects of temperature, increasing size at α-substitution, and by changing the identity of the nucleophile on the selectivity of N,N'-2,5-DKP cyclization, in accordance with embodiments of the present disclosure.

A controlled set of experiments to gauge the effects of temperature, increasing size at α-substitution, and by changing the identity of the nucleophile on the selectivity of N,N'-2,5-DKP cyclization were performed (as illustrated in FIG. 13). A benzyl ester and a p-tolyl ester were used as comparison to eliminate differences in leaving group ability as well as to gauge selectivity. Initially, isopropylamine was chosen to study the cyclization since it is small. The small nucleophile was used to lessen any steric or electronic interaction between the nucleophile and the ester. Isopropylamine is also small enough to not block a face of an electrophile and prevent attack at the Burni-Dunitz angle.

When no α-substituent was present, no selectivity was observed in the cyclized DKP. A 1:1 mixture of both cyclization products was observed. For compound 17 (illustrated in FIG. 13), the methyl α-substituent changed the selectivity of the cyclization with exclusive attack of the benzyl ester. Since sterics from the nucleophile were minimized and leaving group ability was eliminated, it is logical to suggest that rotameric preference plays a role in selectivity. In compound 17, the rotamer that points the amine in a trajectory towards the benzyl ester is favored at room temperature.

The experiments of FIG. 13 demonstrate increasing α-substitution altered selectivity, presumably through specific steric interactions. The identity of the nucleophile had a significant impact on the selectivity, suggesting sterics and possible electronic interactions between the incoming nucleophile and the ester.

The energy barrier to interconvert between the two rotamers in this system was calculated to be 14 kcal/mol. This suggests that a change in temperature alters the degree of selectivity. Compound 17 cyclized to a more substituted compound 19 with near complete selectivity at room temperature, but favored compound 18 at 90° C. reaction temperature. This suggests that at higher temperature, the trajectory of the amine nucleophile switches towards the p-tolyl ester. This is indicative of a change in the rate of exchange between rotamers.

Even larger α-substituent, such as in compound 20, required 90° C. in order to cyclize. This suggests that the size of the α-substituent also has a significant impact on selectivity. The methyl group in compound 17 was not large enough of a hindrance to prevent cyclization; whereas, the large isopropyl group in compound 20 was large enough. This suggests that, at room temperature, the preferred amide rotamer directs the amine on a trajectory towards an ester that may be blocked from the α-substituent.

Interestingly, compound 20 (in FIG. 13) was a peptoid dimer consisting of an equal ratio of amide rotamers. The energy barrier to interconvert between rotamers, of compound 20, was calculated to be greater than 14 kcal/mol. The cyclization did not occur due to a combination of the size of the α-substitutent and the lack of enough energy to overcome the activation barrier.

At 90° C. the reaction of compound 20 progressed with exclusive attack of the p-tolyl ester. The temperature on rotamers was directly observed in $^1$H NMR at 90° C. through coalescence of peaks. At this temperature, enough energy was present to overcome the activation barrier and allow cyclization. This indicates that even at high temperature, the size of the α-substituent has a significant role in selectivity, even when both rotamers are in equilibrium.

The identity of the nucleophile also has an effect on selectivity. When L-alanine ethyl ester was used instead of isopropylamine to make compounds 23 and 24 (in FIG. 13), the ratio of products changed. Steric interactions from the nucleophile to the ester can slow the cyclization. This would allow both trajectories to occur in competition since the cyclization rate is slowed. This should allow for a mixture of products. Since the size of these nucleophiles is only moderately different, it suggests that small changes in sterics may have a significant impact on selectivity.

Figure 14:
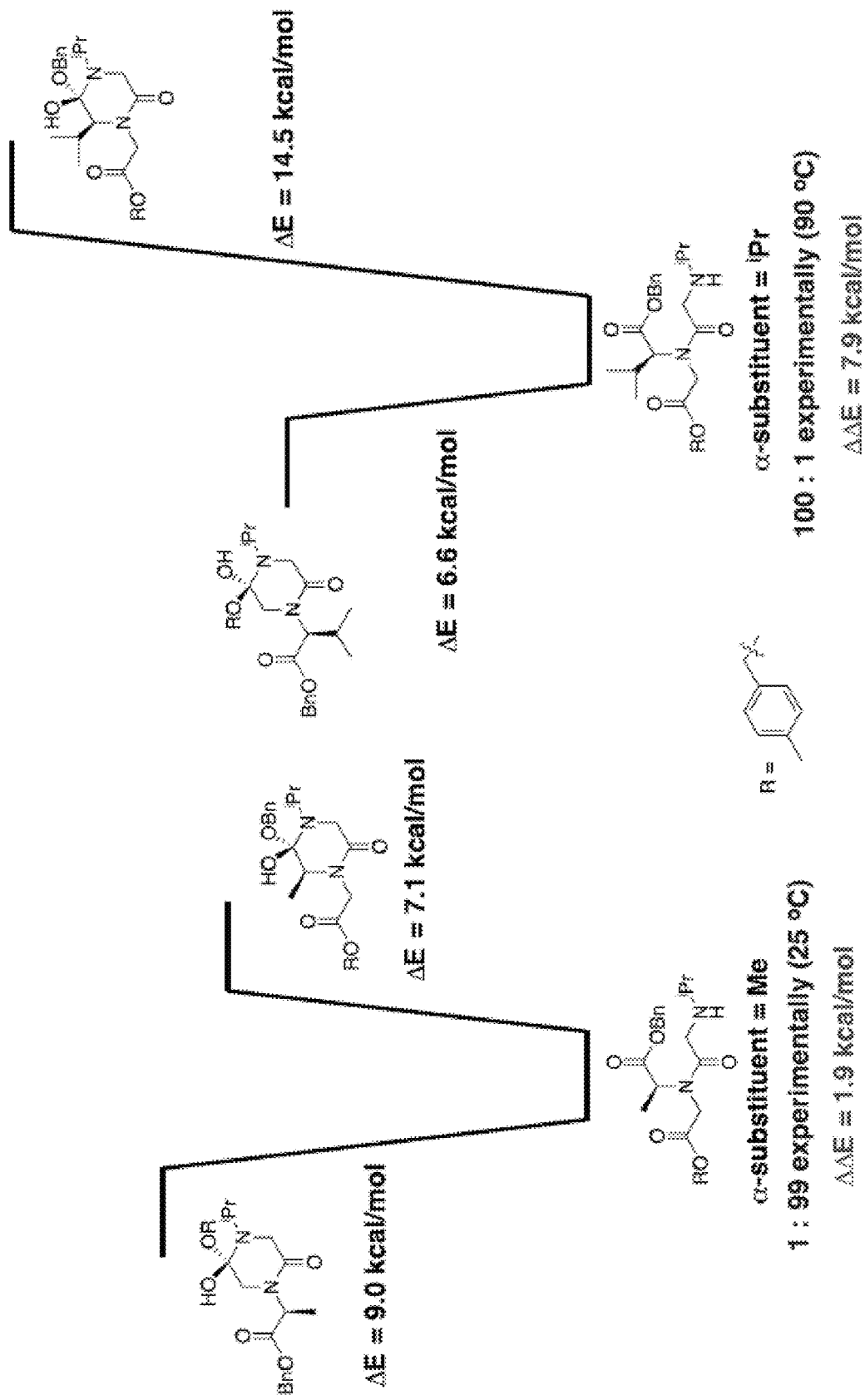
FIG. 14 illustrates energy differences, ΔE, between peptoid dimers and corresponding tetrahedral intermediates, in accordance with embodiments of the present disclosure.

Density functional theory (DFT) optimizations were performed on a number of conformations of peptoid dimers as well as each possible tetrahedral intermediate (as illustrated in FIG. 8). Conformational analysis suggests selectivity based on ΔE differences. The energy levels of the peptoid dimers were determined from averaging several energies of different conformations. The lower energy tetrahedral intermediates are presented in FIG. 14. DFT optimizations of all structures were performed with B3LYP/6-31G** utilizing CPCM solvation model with DMF as the solvent. The result for when α-substituent=H is not shown: the ΔΔE was calculated to be 0.6 kcal/mol and a 1:1 mixture was observed experimentally.

For almost each case, it was observed that the preferred conformation of the tetrahedral intermediate has the alcohol in the axial position. Due to the proximity of the nitrogen atom, this suggests stabilization from the anomeric effect. In addition to the anomeric effect, the large aliphatic groups prefer to be equatorial. The isopropyl group in the axial position is highly disfavored. This high-energy conformation improves selectivity towards the other tetrahedral intermediates.

The experiments suggest selectivity in the cyclization reaction based on energetic differences between linear peptoid dimers and the corresponding tetrahedral intermediates. The energetics between the tetrahedral intermediates towards the experimentally observed product is less endothermic than the energetics towards the unobserved product. This suggests that the activation barrier difference from the peptoid dimer to each DKP warrants selectivity.

Figure 15:
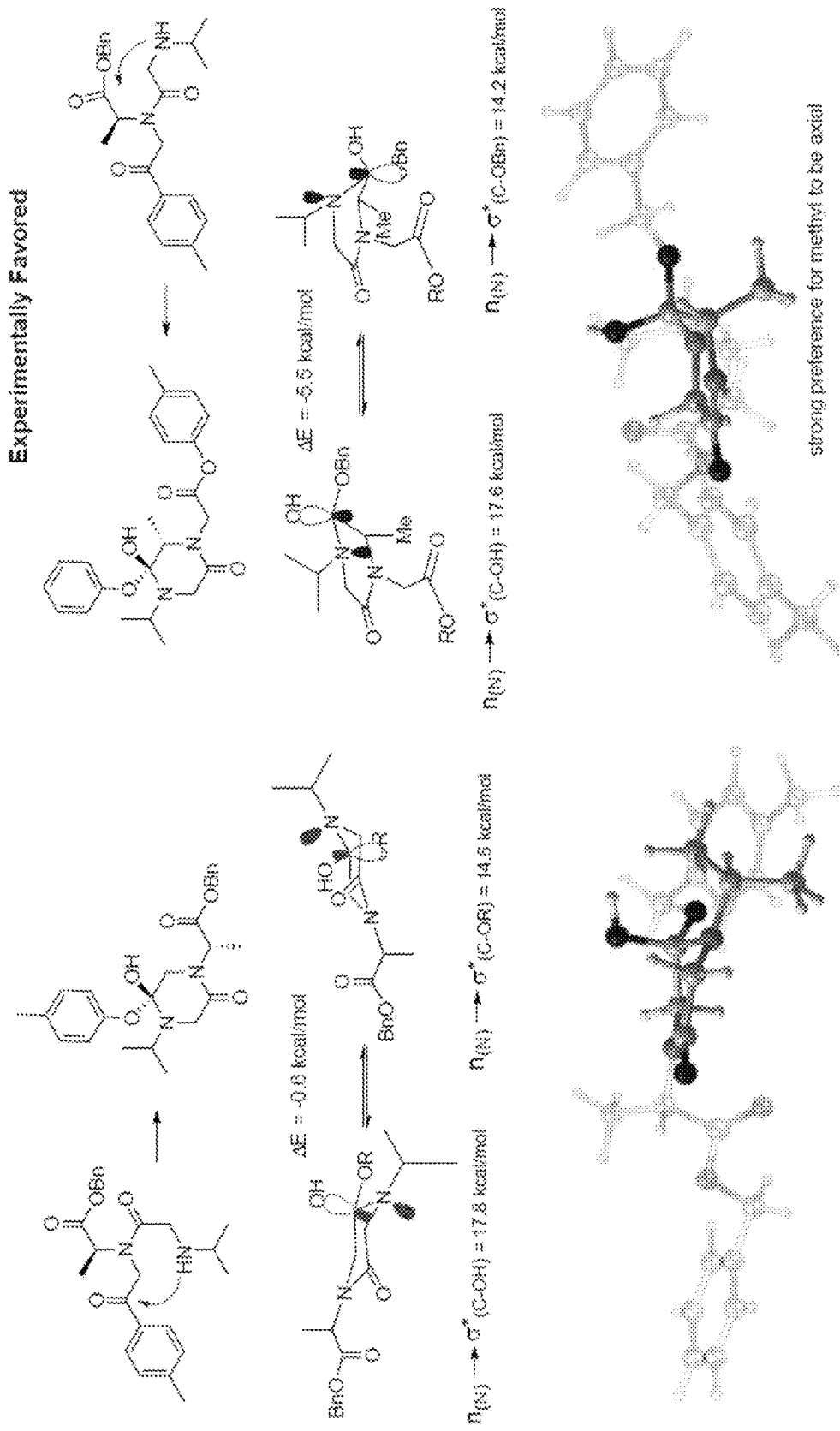
FIG. 15 illustrates conformational analysis of tetrahedral intermediates, in accordance with embodiments of the present disclosure.

Conformational analysis of each tetrahedral intermediate (as illustrated in FIG. 15) suggests that a combination of stereoelectronic effects and minimizing sterics explains why the more substituted DKP was favored at room temperature. The acceptor abilities of the σ*(c–o) were compared when the C—OH was pseudoaxial or the C—OR was pseudoaxial. The C—OH has a moderate preference to be in the axial position by about 3 kcal/mol, based on comparing natural bond orbital (NBO) acceptor ability of the σ*(C—O). For compound 18 (illustrated in the left side of FIG. 15), the energy difference between flipped conformers was calculated to be 0.6 kcal/mol, suggesting fast equilibrium between conformers. For compound 19 (illustrated in the right side of FIG. 15), the energy difference between flipped conformers was calculated to be 5.5 kcal/mol.

Compound 19 prefers to have the endocyclic methyl in the pseudoaxial position. This limits the steric interaction between the endocyclic isopropyl group and the leaving group ester. The anomeric effect enables selective stabilization of the C—OH in the pseudoaxial position over the C—OBn substituent by over a 3 kcal/mol, based on NBO analysis.

A combination of minimizing sterics and stereoelectronics helps explain the inherit selectivity of the cyclization of compound 17.

Overview of Terms and Abbreviations

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the foregoing detailed description and the claims.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that can depend on the desired properties sought and/or limits of detection under standard test conditions/methods.

While the present disclosure has been particularly described in conjunction with specific embodiments, it is evident that many alternatives, modifications, and variations will be apparent to those skilled in the art in light of the foregoing description. It is therefore contemplated that the appended claims will embrace any such alternatives, modifications, and variations as falling within the true spirit and scope of the present disclosure.

What is claimed is:

1. A method for controlling cyclization of peptoids to form chiral diketopiperazines, comprising:
   reacting an acetate ester, comprising a leaving group, with a primary amine to produce a first product having two electrophiles;
   reacting the first product with a haloacetyl halide to produce a second product; and
   reacting the second product with an amine nucleophile to produce an N,N'-2,5-diketopiperazine.

2. The method of claim 1, wherein the leaving group halide is bromine.

3. The method of claim 1, wherein the leaving group is either a mesylate or tosylate leaving group.

4. The method of claim 1, wherein the acetate ester further comprises at least one of an aliphatic group or an aromatic group.

5. The method of claim 4, wherein the at least one of an aliphatic group or an aromatic group comprises at least one of tert-butyl, benzyl, ethyl, or p-tolyl.

6. The method of claim 1, wherein the primary amine is selected from the group consisting of an aliphatic primary amine, an aromatic primary amine, an alkenyl primary amine, an alkynyl primary amine, and an acyl primary amine.

7. The method of claim 1, wherein a functional group, of the primary amine, is protected using at least one of an ester, tert-butoxyl ester (BOC), benzyloxy carbamate (CBz), a silyl ether, or a pivoloyl ester (Piv).

8. The method of claim 1, wherein reacting the acetate ester with the primary amine comprises adding the acetate ester to a solution comprising the primary amine and a tertiary amine.

9. The method of claim 8, wherein the tertiary amine comprises at least one of triethylamine, diisopropylamine, imidazole, diisopropylethylamine, or diazabicyclo[2.2.2]octane (DABCO).

10. The method of claim 8, wherein the solution comprises a solvent comprising at least one of dichloromethane (DCM), acetonitrile, tetrahydrofuran (THF), or N,N'-dimethylformamide (DMF).

11. The method of claim 1, wherein reacting the acetate ester comprises chilling a reaction mixture to about 0° C.

12. The method of claim 1, wherein reacting the first product comprises adding the first product to a solution comprising the haloacetyl halide and at least one of pyridine, triethylamine, or diisopropylethylamine.

13. The method of claim 1, wherein the haloacetyl halide is selected from the group consisting of bromoacetyl bromide, chloroacetyl chloride, and chloroacetyal bromide.

14. The method of claim 1, wherein reacting the first product comprises reacting the first product with a N-hydroxysuccinimide (NHS)-ester of the haloacetyl halide.

15. The method of claim 1, wherein reacting the first product comprises adding the first product to a solution comprising the haloacetyl halide and at least one base.

16. The method of claim 15, wherein the at least one base comprises at least one of a tertiary amine or an aromatic amine.

17. The method of claim 1, wherein reacting the first product comprises chilling a solution, comprising the first product and the haloacetyl halide, to about 0° C.

18. The method of claim 1, further comprising:
producing a charged intermediate that stirs as a colored slurry in dichloromethane, wherein producing the charged intermediate comprises adding at least one of a tertiary amine or an aromatic amine to a solution comprising the haloacetyl halide,
wherein reacting the first product comprises reacting the first product with the charged intermediate to produce the second product.

19. The method of claim 18, wherein reacting the first product with the charged intermediate is performed until the colored slurry has disappeared.

20. The method of claim 1, wherein the amine nucleophile is a primary amine.

\* \* \* \* \*